(12) United States Patent
Gera et al.

(10) Patent No.: US 8,575,170 B2
(45) Date of Patent: Nov. 5, 2013

(54) FLURBIPROFEN ANALOGS AND METHODS OF USE IN TREATING CANCER

(75) Inventors: Lajos Gera, Denver, CO (US); Daniel C. Chan, Denver, CO (US); Robert S. Hodges, Denver, CO (US); Paul A. Bunn, Denver, CO (US)

(73) Assignee: The Regents of the Unversity of Colorado, a body corporate, Denver, CO (US)

( * ) Notice: Subject to any disclaimer, the term of this patent is extended or adjusted under 35 U.S.C. 154(b) by 20 days.

(21) Appl. No.: 13/035,834

(22) Filed: Feb. 25, 2011

(65) Prior Publication Data
US 2011/0275648 A1 Nov. 10, 2011

Related U.S. Application Data

(60) Provisional application No. 61/308,587, filed on Feb. 26, 2010.

(51) Int. Cl.
*A61K 31/495* (2006.01)
*A61K 31/4453* (2006.01)
*C07D 295/15* (2006.01)

(52) U.S. Cl.
USPC ....... 514/252.12; 514/331; 544/400; 546/234

(58) Field of Classification Search
USPC .............. 514/252.12, 331; 544/400; 435/375; 546/234
See application file for complete search history.

(56) References Cited

U.S. PATENT DOCUMENTS

| | | | |
|---|---|---|---|
| 6,770,656 B2 | 8/2004 | Halazy et al. | |
| 7,071,168 B2 | 7/2006 | Stewart et al. | |
| 7,109,243 B2 * | 9/2006 | Liu et al. | 514/595 |
| 2006/0019900 A1 | 1/2006 | Lam et al. | |
| 2008/0269282 A1 | 10/2008 | Clauzel et al. | |

FOREIGN PATENT DOCUMENTS

WO    WO 0059874 A1 * 10/2000 ............ C07C 259/06

OTHER PUBLICATIONS

Vaya et al., Excited-State Interactions in Flurbiprofen-Tryptophan Dyads, 2007, J. Phys. Chem. B, 111, 9363-9371.*
Mishra et al., Synthesis, characterization and pharmacological evalutaion of amide prodrugs of Flurbiprofen, 2008, J. Braz. Chem. Soc., 19 (1), 89-100.*
International Search Report from related PCT Patent Application No. PCT/US2011/026345 mailed Apr. 12, 2011.

* cited by examiner

*Primary Examiner* — Kristin Vajda
(74) *Attorney, Agent, or Firm* — Sheridan Ross P.C.

(57) ABSTRACT

Flurbiprofen analog compounds having an amino acid derivatized at the flurbiprofen alkanoic acid carboxyl group and terminating at an ester or amide group are effective in inhibiting cancer cells in vitro and inhibiting the growth of cancers in viva. The compounds and pharmaceutical compositions containing them are particularly useful for the treatment of lung, pancreatic and head and neck cancers.

17 Claims, 12 Drawing Sheets

FLURBIPROFEN ANALOGS AND METHODS OF USE IN TREATING CANCER

This application claims the benefit of U.S. Provisional Application No. 61/308,587, filed Feb. 26, 2010, which is incorporated herein by reference in its entirety.

GOVERNMENT INTEREST

This invention was made with Government support under grant number CA058187 awarded by the National Institutes of Health (NIH). The Government has certain rights in this invention.

FIELD OF THE INVENTION

The present invention relates to flurbiprofen analogs and their use in treating cancers, including lung-cell, head and neck, and pancreatic cancers.

BACKGROUND OF THE INVENTION

Adenocarcinoma, arising from the bronchial mucosal glands, is the most frequent non-small cell lung cancer in the United States, representing 35-40% of all lung cancers and usually occurs in a peripheral location within the lung. Adenocarcinoma is the most common histologic subtype, and may manifest as a "scar carcinoma." This is the subtype observed most commonly in persons who do not smoke and may manifest as multifocal tumors in a bronchoalveolar form.

Bronchoalveolar carcinoma is a distinct subtype of adenocarcinoma with a classic manifestation as an interstitial lung disease on chest radiograph. Bronchoalveolar carcinoma arises from type II pneumocytes and grows along alveolar septa. This subtype may manifest as a solitary peripheral nodule, multifocal disease, or a rapidly progressing pneumonic form. A characteristic finding in persons with advanced disease is voluminous watery sputum.

Squamous cell carcinoma accounts for 25-30% of all lung cancers. The classic manifestation is a cavitary lesion in a proximal bronchus. This type is characterized histologically by the presence of keratin pearls and can be detected based on results from cytologic studies because it has a tendency to exfoliate. It is the type most often associated with hypercalcemia.

Large cell carcinoma accounts for 10-15% of lung cancers, typically manifesting as a large peripheral mass on chest radiograph. Histologically, this type has sheets of highly atypical cells with focal necrosis, with no evidence of keratinization (typical of squamous cell carcinoma) or gland formation (typical of adenocarcinomas).

SUMMARY OF THE INVENTION

The invention includes, in one aspect, a flurbiprofen analog compound having the structural formula:

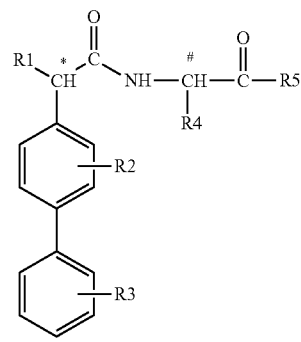

including pharmaceutically acceptable salts and prodrugs thereof, where $R_1$ is selected from H or a 1-4 carbon alkyl, $R_2$ is selected from F, Cl, and Br and may include two or more $R_2$ substitutions on the ring, $R_3$ is selected from H, F, Cl and Br, and may include two or more non-H substitutions on the ring, —NH—CH($R_4$)—C(O)— is a hydrophobic amino acid, and C(O)$R_5$ is an amide or ester.

In various exemplary embodiments, —NH—CH($R_4$)—C(O)— may be selected from one of L-(4-Phenylphenyl)alanine (Bip), L-3,3-Diphenylalanine (Dip), O-(2,6-dicholorbenzyl)-L-tyrosine (OC2Y), L-3-(2-Naphthyl)alanine (2Nal), L-3-Benzothienylalanine (Bta), L-β-Cyclohexylalanine (βCha), L-3-Pyridylalanine (3Pal), β-(p-Biphenylyl)-β-alanine (βBpa), L-4-Trifluoromethylphenylalanine (F3MF), L-Fluorophenylalanine (PFF), and L-Melphalane (MEL).

C(O)$R_5$ may be an amide that terminates in an H atom or a 1-6 carbon linear, branched or cyclic alkyl or alkenyl group, including cyclic groups with one or more nitrogen, oxygen or sulfur ring atoms. In an exemplary embodiment, $R_5$ may be 1-(3-Aminopropyl)-4-methylpiperazine (Amp) or 4-Amino-2,2,6,6-tetramethylpiperidine (Atmp).

$R_2$ may be a single meta-position F, $R_3$ may be H, and $R_4$ may be $CH_3$.

In one general embodiment, the flurbiprofen analog compound has the structure

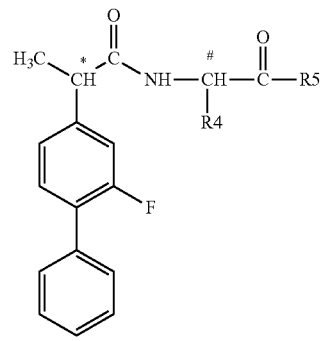

where —NH—CH($R_4$)—C(O)— may be selected from one of L-(4-Phenylphenyl)alanine) (also called L-4,4'-Biphenylalanine, or Bip), L-3,3-Diphenylalanine (Dip), O-(2,6-dicholorbenzyl)-L-tyrosine (OC2Y), L-3-(2-Naphthyl)alanine (2Nal), L-3-Benzothienylalanine (Bta), L-β-Cyclohexylalanine(βCha), L-3-Pyridylalanine (3 Pal), β-(p-Biphenylyl)-β-alanine (βBpa), L-4-Trifluoromethylphenylalanine (F3MF), L-Fluorophenylalanine (PFF), and L-Melphalane (MEL), and $R_5$ may be 1-(3-Aminopropyl)-4-methylpiperazine (Amp) or 4-Amino-2,2,6,6-tetramethylpiperidine (Atmp).

The compound may be a pure R or pure S enantiomer or an RS racemic mixture at chiral position * and a pure L or pure D enantiomer or an LD racemate at the chrial position #. In one exemplary embodiment, the compound is a pure S enantiomer at the * chiral position, and a pure L enantiomer at the chiral position #.

The compound may be formulated as a pharmaceutical composition in a pharmaceutically acceptable medium suitable for oral or parenteral administration.

In another aspect, the invention provides a method of inhibiting cancer cells by exposing the cells to an inhibitory concentration of the flurbiprofen analog compound above. The compound is preferably one cable of producing a 50% inhibition of cell viability at a concentration between 0.1 and 10 µM. The cancer cell line that is inhibited may be selected from a lung, head and neck, and pancreatic cell line. The flurbiprofen analog compound to which the cells are exposed may be one of the exemplary compounds noted above.

In still another aspect, the invention includes a method of treating a solid tumor in a mammalian subject, by administering to the subject, a therapeutically effective amount of the flurbiprofen analog compound above, and repeating the administration at intervals of at least twice per week for a period of at least four weeks.

The compound may be administered on a daily basis at a daily dose between 1 to 25 mg/kg body weight. The compound may be administered orally, intraperitoneally, intravenously, subcutaneously, by inhalation, by transdermal administration or trans-mucosal delivery The method may further include administering to the patient, a second cancer therapy regimen selected from radiotherapy and one or more other chemotherapeutic compounds. Administering the flurbiprofen analog compound may be effective to potentiate the effect of the second cancer therapy regimen.

The flurbiprofen analog compound administered may be one of the exemplary compounds noted above.

For treatment of pancreatic or lung cancer, the compound may be administered at a daily dose between 1 and 25 mg/kg body weight of the compound over a period of at least five weeks.

These and other objects and features of the invention will be more fully understood from the following detailed description of the invention when read in conjunction with the accompanying figures.

DETAILED DESCRIPTION

I. Definitions

Figure 1:
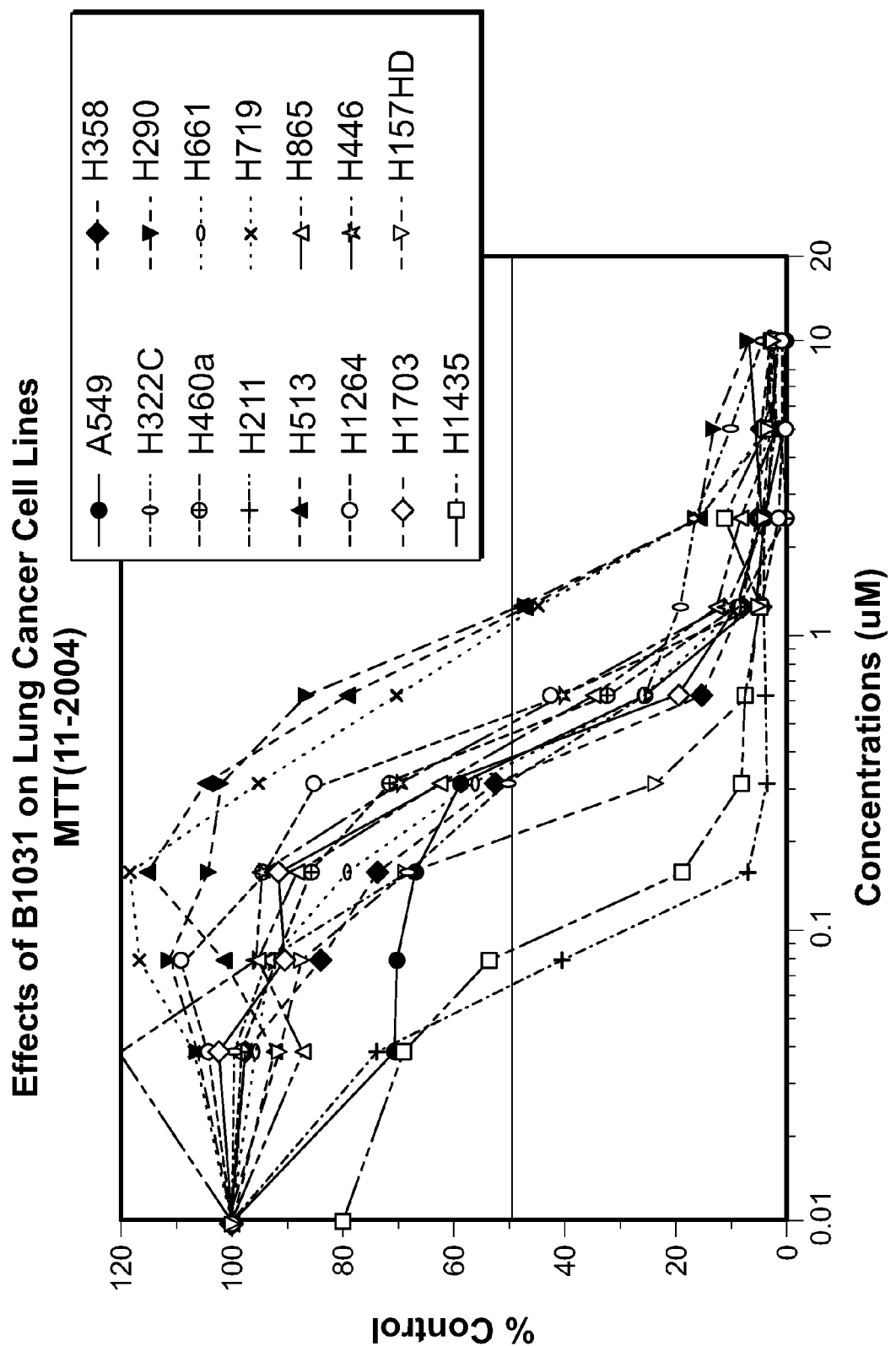
FIG. 1 shows cell survival of 15 cancer cell lines following treatment with N—[(S)-2-Fluoro-α-methyl-4-biphenylacetyl]-[L-(4-phenylphenyl)alanine]-N'-(2,2,6,6-tetramethyl-4-piperidinyl)amide (GCBH-110=B1031) using an MTT cell-viability assay.

The terms below have the following definitions unless indicated otherwise:

"Flurbiprofen analog compound" means a compound having a flurbiprofen parent structure that may contain halide substitutions at one or both phenyl rings, alkyl substitutions at its carbon alkanoic acid group, and which is derivatized at its carboxyl alkanoic acid group to an amino acid that itself terminates at an ester or amide group.

Flurbiprofen has a single chiral center at the alkanoic acid carbon position, designated herein as "*", and a single chiral center at the alpha carbon position of the amino acid, designated "#". At each of these positions, the compound lacks an internal plane of symmetry and has two non-superposable mirror images. The two stereoisomers at each position are commonly referred to as enantiomers, and a mixture of the two enantimoers, as a racemate. The enantiomers at the alkanoic carbon position of flurbiprofen are referred to as R and S enantiomers, and the enantiomers at the alpha carbon of the amino acid as L and D enantiomers.

The "—NH—CH($R_4$)—C(O)" amino acid moiety in the flurbiprofen analog compound may be one in which the $R_4$ group is attached to the alpha carbon of the amino acid having a given L or D isomeric configuration, in which case the compound will have the L, D, or LD stereochemistry of the amino acid backbone, or one in which the $R_4$ group is attached to, for example, the beta carbon in beta alanine, in which —NH—CH(R$_4$)—C(O) may be a mixture of L and D enantiomers.

"Pharmaceutically-acceptable salts" refer to derivatives of the disclosed compounds in which the parent compound is modified by making acid or base salts thereof. Examples of pharmaceutically-acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically-acceptable salts are those forms of compounds, suitable for use in contact with the tissues of human beings and animals without causing excessive toxicity, irritation, allergic response, or other problems or complication, commensurate with a reasonable benefit/risk ratio.

"Prodrugs" are considered to be any covalently bonded carriers, which release the active parent anti-cancer compound of the present invention in vivo when such prodrug is administered to a mammalian subject. Prodrug forms of the compounds of the present invention are prepared by modifying functional groups present in the compounds in such a way that the modifications are cleaved, either in routine manipulation or in vivo, to the parent compounds. Prodrug forms include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of the present invention, and the like. Compounds that function effectively as prodrug forms of the compounds of the present invention may be identified using routine techniques known in the art. For examples of such prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8, 1-38 (1992); d) H. Bundgaard, et al., Journal of Pharmaceutical Sciences, 77:285 (1988); and e) N. Kakeya, et al., Chem. Pharm. Bull., 32: 692 (1984), each of which is specifically incorporated herein by reference.

The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of the present invention, including compounds produced by a process comprising contacting a compound of this invention with a mammal for a period of time sufficient to yield a metabolic product thereof.

The term "therapeutically effective amount" of a compound of this invention means an amount effective to prevent, treat, kill, reduce the growth or inhibit the malignant phenotype of neoplastic cells in a mammalian host.

II. Flurbiprofen Analog Compounds and Compositions

The present invention is directed to anticancer compounds derived from flurbiprofen and the use of these compounds to treat cancer cells and patients diagnosed with a cancer. The compound has the general structural formula:

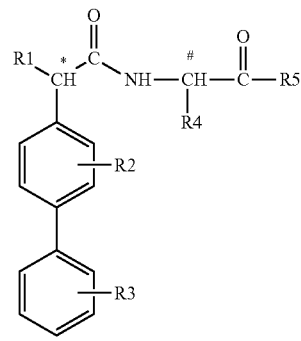

where $R_1$ is a selected from H or a 1-4 carbon alkyl, $R_2$ is selected from F, Cl, and Br and may include two or more $R_2$ substitutions on the ring, $R_3$ is selected from H, F, Cl and Br, and may include two or more non-H substitutions on the ring, —NH—CH($R_4$)—C(O)— is a hydrophobic amino acid, and C(O)$R_5$ is an amide or ester. The compound of the invention also includes pharmaceutically acceptable salts and prodrugs.

The compound may be a pure R or S enantiomer or an RS racemic mixture at the chiral positions * and a pure L or pure D enantiomer or an LD racemate at the chiral position #. The —NH—CH($R_4$)—C(O)— is any hydrophobic amino acid, including both natural and modified amino acids, as illustrated by the following list of exemplary amino acids:

Ac6c 1-Aminocyclohexanecarboxylic acid
AcH 2-Amino-1-cyclohexanecarboxylic acid
AcP 2-Amino-1-cyclopentanecarboxylic acid
APa p-Aminophenylacetic acid
Arg Arginine
Atc 2-aminotetraline-2-carboxylic acid
Bip 4,4'-Biphenylalanine or (4-Phenylphenyl)alanine
ChG α-Cyclohexylglycine
CpG α-Cyclopentyglycine
βBpa β-(p-Biphenylyl)-β-alanine
BtA 3-Benzothienylalanine
Dip 3,3-Diphenylalanine
DmK ε-Dimethyllysine
F3MF 4-Trifluoromethylphenylalanine
F5F Pentafluorophenylalanine
Ica Indoline-2-carboxylic acid
Igl α-2-Indanylglycine
MEL Melphalane
1Nal 3-(1-Naphthyl)alanine
2Nal 3-(2-Naphthyl)alanine
NiK ε-Nicotinoyllysine
NMF N-Methylphenylalanine
OBPY O-Benzyl-phosphotyrosine
OC2Y O-(2,6-Dichlorobenzyl)tyrosine
OCIY O-(2,6-Dichlorobenzyl)-3,5-diiodotyrosine
Oic Octahydroindolecarboxylic acid Pac 4-Aminocinnamic acid
2 Pal 2-Pyridylalanine
3 Pal 3-Pyridylalanine
4 Pal 4-Pyridylalanine
Pen(Mbzl) S-(4-Methylbenzyl)-penicillamine
PaF p-Amino-phenylalanine
PBF p-Bromo-phenylalanine
PCNF p-Cyano-phenylalanine
PgF p-Guanidino-phenylalanine
Phe Phenylalanine
PIF p-Iodo-phenylalanine
PipA β-3-Piperidylalanine
2Qua 2-Quinoylalanine
2,4Tfp 2,4-Bis(trifluoromethyl)-phenylalanine
3Tfp 3,5-Bis(trifluoromethyl)-phenylalanine
Tic Tetrahydroisoqunoline-3-carboxylic acid
Thi β-(2-Thienyl)-alanine
TmK ε-Trimethyllysine
Trp Tryptophan
Tza 4-Thiazolylalanine In one general embodiment, the $C(O)R_5$ is an amide that terminates in an H atom or a 1-6 carbon linear, branched or cyclic alkyl or alkenyl group, including cyclic groups with one or more nitrogen, oxygen or sulfur ring atoms. Exemplary $R_5$ groups include include:
Abzp 4-Amino-1-benzylpiperidine
Acep 4-Amino-1-carbethoxymethyl-2,2,6,6-tetramethylpiperidine
Ambi 2-(Aminomethyl)benzimidazole
Amp 1-(3-Aminopropyl)-4-methylpiperazine
Apia 4-Amino-piperidine
Aptp 4-Amino-1-(phenylmethyl)-2,2,6,6-tetramethylpiperidine
Atmp 4-Amino-2,2,6,6-tetramethylpiperidine
AtmpO 4-Amino-2,2,6,6-tetramethyl-1-piperidinyloxy
Atpc 4-Amino-2,2,6,6-tetramethyl-4-piperidinecarboxylic acid
Atpm 4-Amino-4-methoxycarbonyl-2,2,6,6-tetramethylpiperidine
Aqd 4-Aminoquinaldine
Aqu (R)-(+)-3-Aminoquinuclidine or (S)-(−)-3-Aminoquinuclidine
Bhp 1-Benzylhomopiperazine
Btpha N,N'-Bis(2,2,6,6-tetramethyl-4-piperidinyl)-1,6-hexanediamine
cDmbp cis-2,6-Dimethyl-1-benzylpiperazine
Dabp Diethyl 4-aminobenzylphosphonate
DCE N,N'-Bis(2-chloroethyl)ethylenediamine
Dcpp 1-(2,3-Diclorophenyl)piperazine
Dmm 2,6-Dimethylmorpholine
Dmmp cis-2,6-Dimethyl-1-(methoxycarbonylmethyl)piperazine)
Ecap N-(Ethoxycarbonyl)-4-aminopiperidine
NH—OH Hydroxylamine
$HN(CH_3)(OCH_3)$ N,O-Dimethylhydroxylamine
Mapp 4-(Methylamino)-1,2,2,6,6-pentamethylpiperidine
Matp 4-(Methylamino)-2,2,6,6-tetramethylpiperidine
MatpO 4-(Methylamino)-2,2,6,6-tetramethyl-1-piperidinyloxy
Pipz piperazine
Pmpz 1-(2-Pyrimidyl)piperazine
Pxa Pyridoxamine
Sua Sulfanilamide
tCip trans-1-Cinnamylpiperazine
Tpac N-(2-aminoethyl)-2,2,5,5-tetramethyl-3-pyrroline-3-carboxamide IIA. Exemplary Compounds The following are exemplary compounds of the invention:

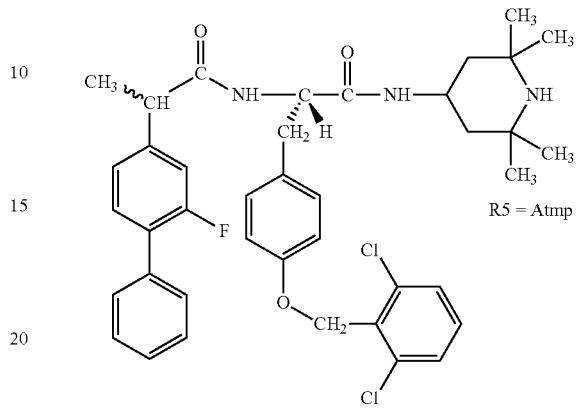

GCBH-100

Fmba-OC2Y-Atmp
N-[(R,S)-2-Fluoro-α-methyl-4-biphenylacetyl]-[O-(2,6-dichlorobenzyl)-L-tyrosine]-N-(2,2,6,6-tetramethyl-4-piperidinyl)amide

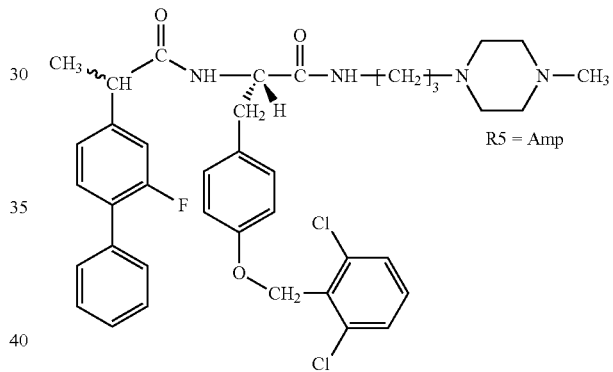

GCBH-102

Fmba-OC2Y-Atmp
N-[(R,S)-2-Fluoro-α-methyl-4-biphenylacetyl]-[O-(2,6-dichlorobenzyl)-L-tyrosine]-N-[3-(4-methyl-1-piperazinyl)propyl]amide GCBH-104=B1005, having the chemical name: N—[(R,S)-2-Fluoro-α-methyl-4-biphenylacetyl]-[L-(4-phenylphenyl)alanine]-N-(2,2,6,6-tetramethyl-4-piperidinyl)amide.

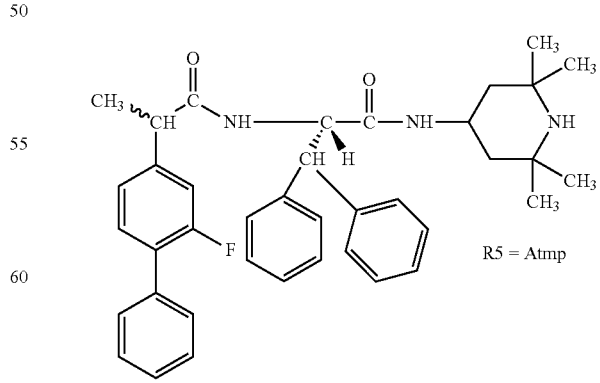

GCBH-106            Fmba-Dip-Atmp
N-[(R,S)-2-Fluoro-a-methyl-4-biphenylacetyl]-(β-phenyl-L-phenyialanine)-N-(2,2,6,6-tetramethyl-4-piperidinyl)amide GCBH-108=B1020 having the chemical name: N—[(R)-2-Fluoro-α-methyl-4-biphenylacetyl]-[L-(4-phenylphenyl)alanine]-N-(2,2,6,6-tetramethyl-4-piperidinyl)amide (R)-Fmba-L-Bip-Atmp.

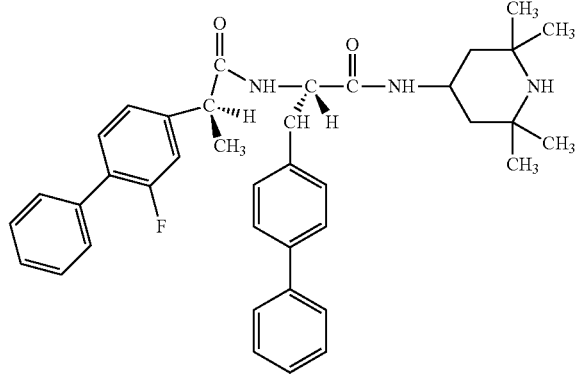

GCBH-10 (S)-Fmba-(S)-Bip-Atmp
N-[(S)-2-Fluoro-a-methyl-4-biphenylacetyl]-[L-(4-[phenyphenyl)alanine]enyialanine)-N-(2,2,6,6-tetramethyl-4-piperidinyl)amide GCBH-110 is also referred to herein as B1031=GH501.

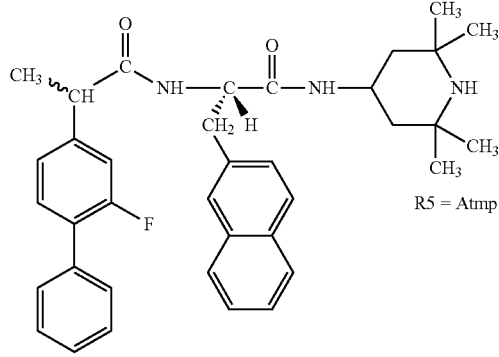

Fmba-2Nal-Atmp
N-[(R,S)-2-Fluoro-α-methyl-4-biphenylacetyl]-[L-β-(2-naphthyl)alanine]-N-(2,2,6,6-tetramethyl-4-piperidinyl)amide

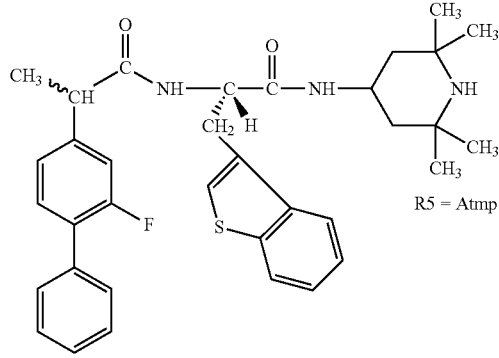

Fmba-Bta-Atmp
N-[(R,S)-2-Fluoro-α-methyl-4-biphenylacetyl]-[L-3-benzothienylalanine]-N-(2,2,6,6-tetramethyl-4-piperidinyl)amide -continued

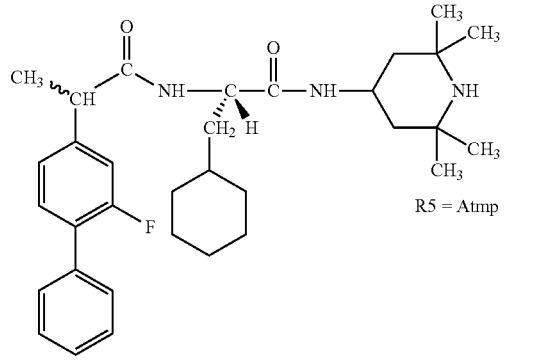

Fmba-betaCha-Atmp
N-[(R,S)-2-Fluoro-α-methyl-4-biphenylacetyl]-(β-cyclohexyl-L-alanine]-N-(2,2,6,6-tetramethyl-4-piperidinyl)amide

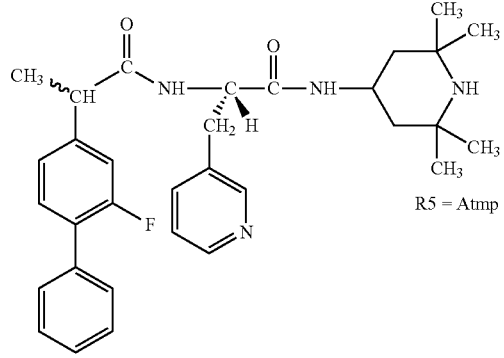

Fmba-3Pal-Atmp
N-[(R,S)-2-Fluoro-α-methyl-4-biphenylacetyl]-(β-3-pyridyl-L-alanine]-N-(2,2,6,6-tetramethyl-4-piperidinyl)amide

GCBH-120

(S)-Fmba-betaBpa-Atmp
N-[(S)-2-Fluoro-α-methyl-4-biphenylacetyl]-[(R,S)-β-(p-biphenylyl)-β-alanine]-N-(2,2,6,6-tetramethyl-4-piperidinyl)amide

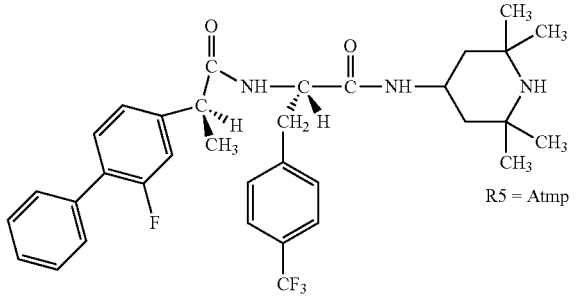

(S)-Fmba-F3MF-Atmp
N-[(S)-2-Fluoro-α-methyl-4-biphenylacetyl]-[(4-trifluoromethyl)-L-phenylalanine]-N-(2,2,6,6-tetramethyl-4-piperidinyl)amide

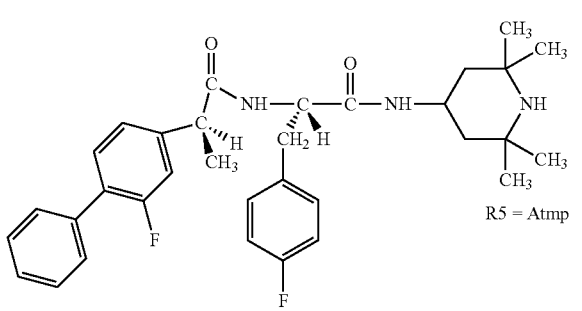

(S)-Fmba-PFF-Atmp
N-[(S)-2-Fluoro-α-methyl-4-biphenylacetyl]-[(4-fluoro)-L-phenylalanine]-N-(2,2,6,6-tetramethyl-4-piperidinyl)amide

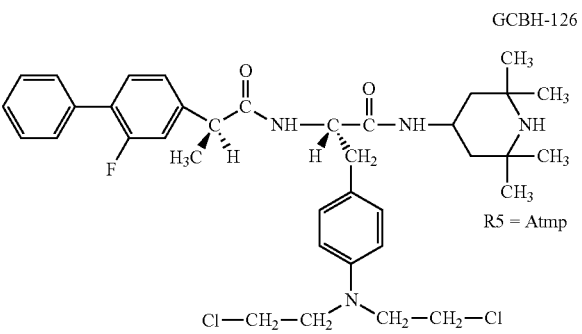

(S)-Fmba-MEL-Atmp
N-[(S)-2-Fluoro-α-methyl-4-biphenylacetyl]-[(4-bis(2-chloroethyl)amino-L-phenylalanine-(2,2,6,6-tetramethyl-4-piperidinyl)amide

IIB. Methods of Synthesis

The compounds of the present invention can be synthesized using the methods described in Examples 2A and 2B below, together with synthetic methods known in the art of organic chemistry, or variations thereon as appreciated by those skilled in the art. In each step of preparing the compounds of the present invention, the amino acid derivatives are coupled to the amine derivatives by BOP or HATU in organic solvent to afford the amide derivatives of residue 2-3 (Boc-2-3). The Boc-groups were cleaved by 25% trifluoroacetic acid (TFA) in DCM and the amino acid-amide derivatives of residues 2-3 were acylated with the appropriate flurbiprofins (Fmba-s) or their derivatives in the presence of BOP to give the flurbiprofen amide analogs of residues 2-3. A simple extraction is used for the isolation and purification of each intermediate (Boc-2-3 and 2-3). The final products are purified by crystallization or preparative high pressure liquid chromatography (HPLC) and may be characterized by analytical HPLC, thin layer chromatography (TLC) and laser-desorption mass spectrometry (LDMS). In the specific instance in which the H groups represent alcohol, the 2-3 amino esters are acylated directly with the flurbiprofins and their derivatives to give Flurbiprofen-2-3.

Examples of the synthesis of the compounds of this invention are described in Example 1 of this disclosure. The reactions are performed in solvents appropriate to the reagents and materials employed and suitable for the transformation being effected. Also, in the description of the synthetic methods described below, it is to be understood that all proposed reaction conditions, including the choice of solvents, reaction temperature, duration of the experiments and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions on the use of substituents that are compatible with the reaction conditions will be readily apparent to one skilled in the art and alternate methods must then be used.

Examples of the synthesis of the compounds of this invention are described in Examples 1A and 1B below, where Example 1A details the synthesis of the above GCBH-110 compound, and Example IIB, modifications to that synthesis for synthesizing the compounds GCBH-100, GCBH-102, GCBH-104, GCBH-106, GCBH-110, GCBH-112, GCBH-114, GCBH-116, GCBH-118, GCBH-120, GCBH-122, GCBH-124, and GCBH-126 shown above.

The reactions are performed in solvents appropriate to the reagents and materials employed and suitable for the transformation being effected. Also, in the description of the synthetic methods described below, it is to be understood that all proposed reaction conditions, including the choice of solvents, reaction temperature, duration of the experiments and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions on the use of substituents that are compatible with the reaction conditions will be readily apparent to one skilled in the art and alternate methods must then be used.

Pharmaceutically-acceptable salt forms of compounds provided herein are synthesized from the parent compound which contains a basic or acidic moiety by conventional chemical methods. Generally, such salts are prepared, for example, by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is incorporated herein by this reference.

IIC. Pharmaceutical Compositions

The compounds of the invention are effective in treating diseases over a wide dosage range and are generally administered in a therapeutically-effective amount. The dosage and manner of administration will be defined by the application of the compound and can be determined by routine methods of clinical testing to find the optimum dose. These doses are expected to be in the range of 0.001 mg/kg to 100 mg/kg of active compound. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

When employed as pharmaceuticals, the compounds of the present invention are administered in the form of pharmaceutical compositions and these pharmaceutical compositions represent further embodiments of the present invention. These compounds can be administered by a variety of routes including oral, rectal, transdermal, subcutaneous, intravenous, intramuscular, and intranasal, or via intratracheal instillation or aerosol inhalation.

The pharmaceutical compositions of the present invention contain, as the active ingredient, one or more of the anti-cancer compounds described above, associated with pharmaceutically acceptable formulations. In making the compositions of this invention, the active ingredient is usually mixed with an excipient, diluted by an excipient or enclosed within a carrier, which can be in the form of a capsule, sachet, paper or other container, according to well-known methods and pharmaceutical compositions.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

III. Method of Inhibiting Cancer Cells

In one aspect, the invention includes a method of inhibiting cancer cells by exposing the cells to an inhibitory concentration of the flurbiprofen compound of the invention. The data presented in Section IIIA below demonstrate that the method is effective against a wide variety of cancer cells associated with both non-small and small-cell lung carcinomas cell lines, head and neck cancer cell lines, pancreatic cancer cell lines, a colon cancer line, and brain cancer cell lines. The mechanism by which the compounds inhibit cell survival and growth is discussed in Section IIIB; Section IIIC demonstrates the approximately 100-1,000 fold greater anti-cancer activity of the activity of the compounds relative to flurbiprofen itself.

IIIA. Inhibition of Cancer Cells Types

The ability of the flurbiprofen analog compounds of the invention to inhibit cancer cell growth and survival (viability) in a variety of cancer lines was examined in a standard MTT assay for cell viability, as detailed in Example 2.

Figure 2:
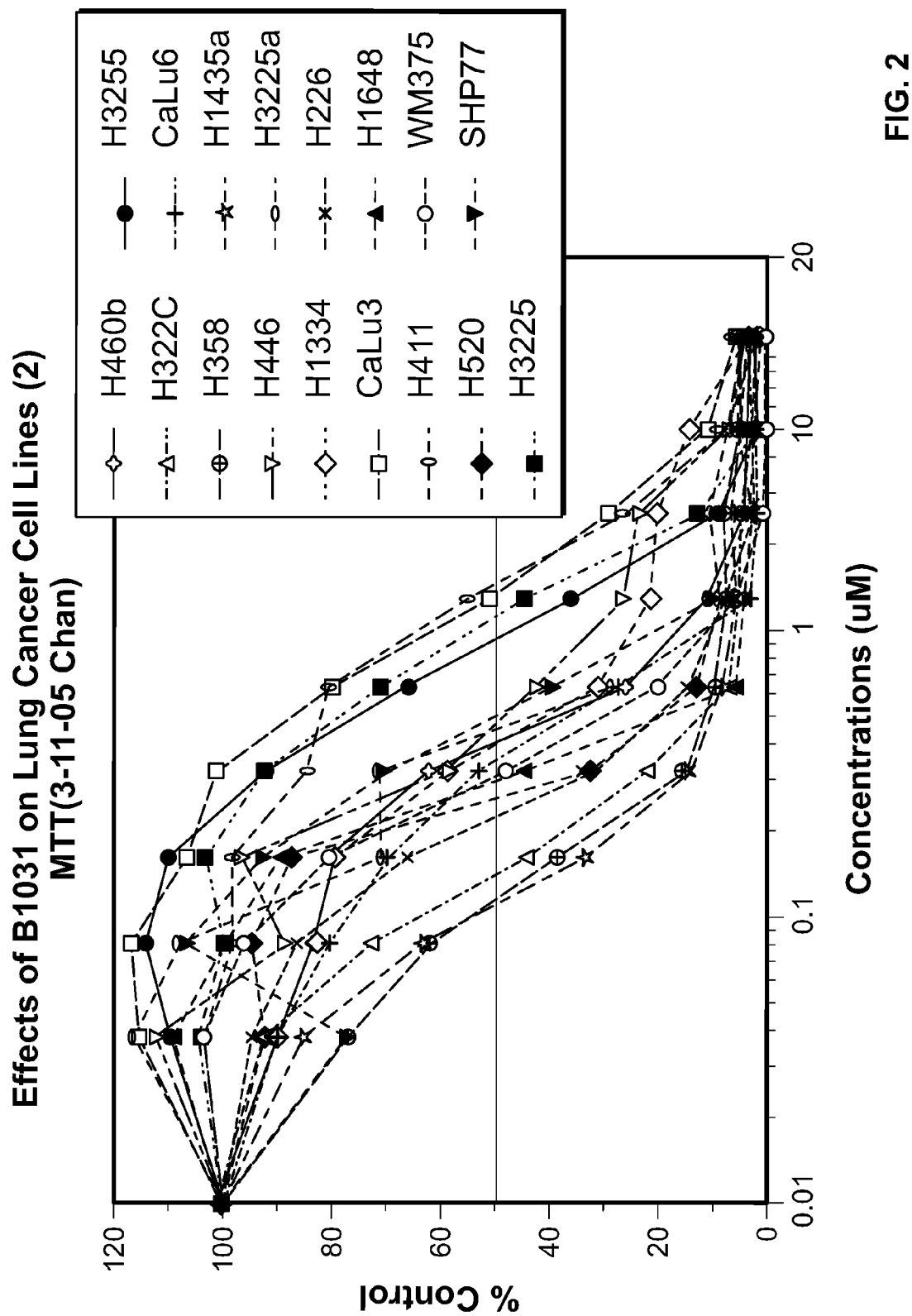
FIG. 2 shows cell survival of 17 lung cancer cell lines following treatment with N—[(S)-2-Fluoro-α-methyl-4-biphenylacetyl]-[L-(4-phenylphenyl)alanine]-N'-(2,2,6,6-tetramethyl-4-piperidinyl)amide (GCBH-110=B1031; (S)-Fmba-(L)-Bip-Atmp) using an MTT cell-viability assay.

In one group of studies, the effect of compound B1031 (compound GCBH-110 above) on a variety of lung cancer cells lines identified in Tables 1A-1C was investigated FIGS. 1 and 2 are dose-response curves, showing the change in percent survival as a function of compound concentration, after four days incubation in the presence of the compound for the various cell lines tested (identified in Tables 1A-1C below). As seen from the figures, compound concentrations in the range 0.1 to 2 µM were effective to produce 50% cell death. The $IC_{50}$ values (compound concentration producing 50% survival) for the 32 lung cancer cell lines studies are summarized in Tables 1A-1C below. The 12 cell lines shown in Table 1A are all adenocarcinoma lines, a type of non-small cell lung carcinoma; the 11 cell lines shown in Table 1B, identified as adenosquamous, large cell, mesothelioma, squamous, and squaous mesothelioma, are non-small cell lung carcinoma lines; and the 7 cell lines shown in Table 1C are all small-cell lung carcinoma cell lines. As seen from the three tables, the B1031 compound has a comparable inhibitory effect on a wide variety of both small- and various non-small cell lung carcinomas, yielding $IC_{50}$ values between about 0.1 and 1.8 μM, with most cell lines showing an $IC_{50}$ value of less than about 0.5 μM.

TABLE 1A

| Lung cell lines | Cell | IC50(uM) |
| --- | --- | --- |
| Adenocarcinoma | A549 | 0.55 |
| Adenocarcinoma | H322C | 0.45 |
| Adenocarcinoma | H2122 | 0.15 |
| Adenocarcinoma | H3255 | 0.9 |
| Adenocarcinoma | H358 | 0.4 |
| Adenocarcinoma | H441 | 1.6 |
| Adenocarcinoma | H322C1 | 0.13 |
| Adenocarcinoma | H358 | 0.102 |
| Adenocarcinoma | CaLu3 | 1.3 |
| Adenocarcinoma | H3225 | 1.1 |
| Adenocarcinoma | CaLu6 | 0.34 |
| Adenocarcinoma | H1435a | 0.11 |
| Adenocarcinoma | H3225a | 0.45 |
| Adenocarcinoma | H3255 | 0.91 |

TABLE 1B

| Lung cell lines | Cell | IC50(uM) |
| --- | --- | --- |
| Adenosquamous | H1264 | 0.63 |
| Adenosquamous | H1703 | 0.36 |
| Large Cell | H460 | 0.48 |
| Large Cell | H661 | 0.35 |
| Large Cell | H460b | 0.4 |
| Large Cell | H1334 | 0.4 |
| Mesothelioma | H513 | 1.8 |
| Mesothelioma | H290 | 1.3 |
| Squamous | H157 | 0.21 |
| Squamous | H520 | 0.25 |
| Squamous | H226 | 0.203 |
| Mesothelioma | | |

TABLE 1C

| Lung cell lines | Cell | IC50(uM) |
| --- | --- | --- |
| SCLC | H719 | 1.08 |
| SCLC | H865 | 0.36 |
| SCLC | SHP77 | 0.53 |
| SCLC | H446 | 0.44 |
| SCLC | H417 | 1.4 |
| SCLC | H1648 | 0.28 |
| SCLC | SHP77 | 0.5 |

A similar study was conducted on 14 neck and neck cancer cell lines, identified in Table 2. As seen from the table, and in FIGS. 3 and 4, which plot change in cell survival as a function of drug compound concentration, $IC_{50}$ values were in the range of between 02 and 2 μM for all of the cancer cell lines tested, with a majority of the cell lines showing an $IC_{50}$ value less than 0.5 μM

TABLE 2

| Head and neck cancers | IC50(uM) |
| --- | --- |
| UMSCC10A | 0.2 |
| S84 | 0.23 |
| UMSCC22B | 0.3 |
| 1483 | 0.3 |
| MSK922 | 0.41 |
| MSK922 | 0.41 |
| UMSCC22A | 0.43 |
| UMSCC22A | 0.43 |
| HN31 | 0.54 |

TABLE 2-continued

| Head and neck cancers | IC50(uM) |
| --- | --- |
| HN31 | 0.54 |
| MSK921 | 0.77 |
| UMSCC2 | 0.95 |
| 1586 | 1.5 |
| UMSCC19 | 2 |

Figure 5:
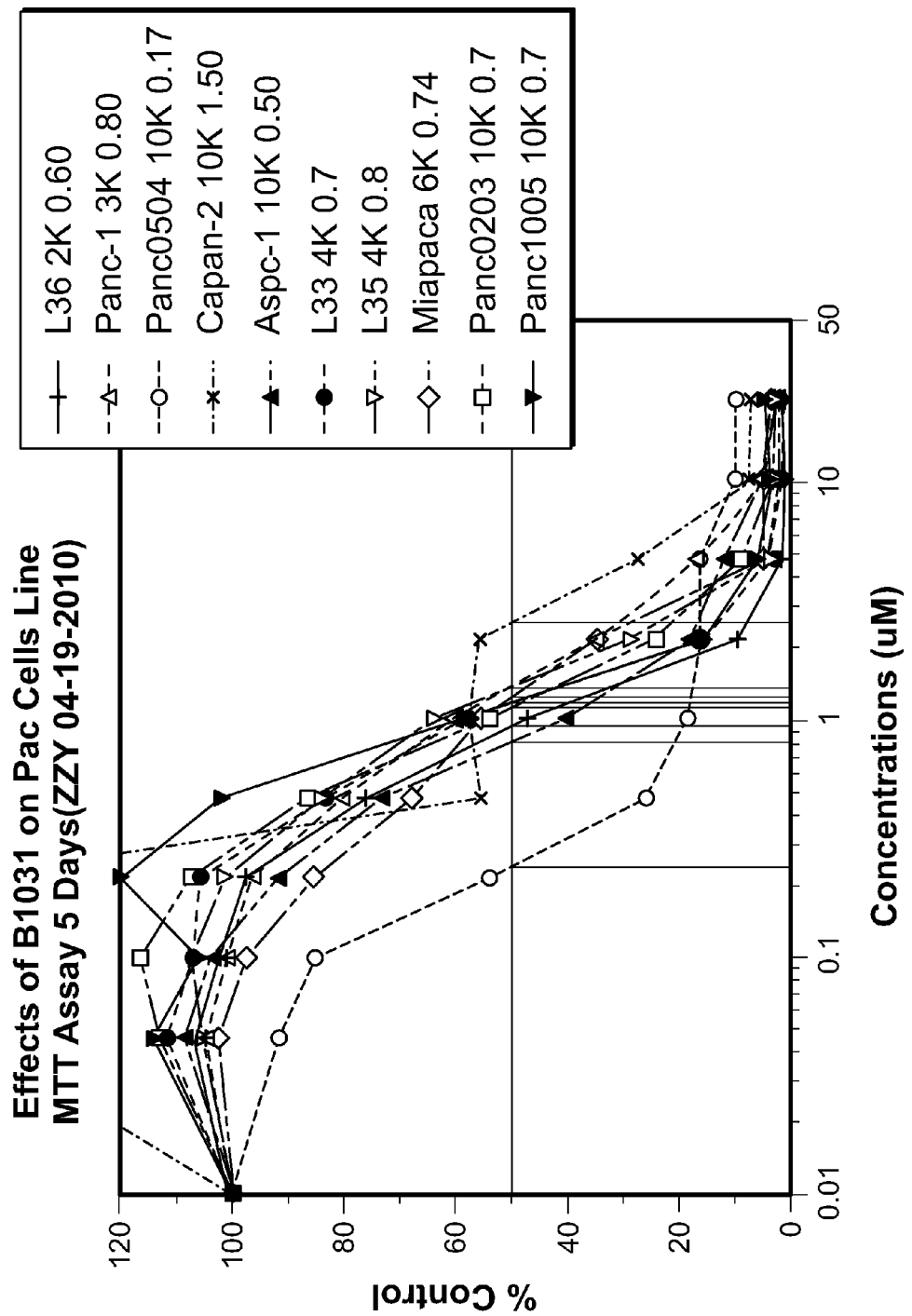
FIG. 5 shows cell survival of 14 pancreatic cancer cell lines following treatment with N—[(S)-2-Fluoro-α-methyl-4-biphenylacetyl]-[L-(4-phenylphenyl)alanine]-N'-(2,2,6,6-tetramethyl-4-piperidinyl)amide (GCBH-110=B1031; (S)-Fmba-(L)-Bip-Atmp) using an MTT cell viability assay.

Similar results were obtained for the effect of the B1031 compound on the 14 pancreatic tumor cells lines shown in Table 3 below, where the dose dependent effect of the compound on survival of the pancreatic cancer cell lines is shown in FIG. 5. As seen in the figure, and in Table 3, IC50 values for cell lines varied between about 0.16 and 3.1 μM, with the majority of the cells lines showing a response of 0.7 μM or below.

TABLE 3

| Pancreatic cancer cells | IC50(uM) |
| --- | --- |
| Panc-504 | 0.16 |
| Aspc-1 | 0.5 |
| L36 | 0.6 |
| Panc-327 | 0.67 |
| L33 | 0.7 |
| Panc-203 | 0.7 |
| Panc-1005 | 0.7 |
| HADF-2 | 0.7 |
| MiaPaCa | 0.74 |
| L35 | 0.8 |
| Panc-1 | 0.81 |
| Capan-2 | 1.5 |
| SW1990 | 1.5 |
| Panc-813 | 3.1 |

The results for the several cell lines above were also consistent with $IC_{50}$ values measured for two melanoma cell lines shown in Table 4 below.

TABLE 4

| Melanoma cell lines | Cell | IC50(uM) |
| --- | --- | --- |
| Melanoma | WM375 | 0.28 |
| Melanoma | WM239a | 0.23 |

Figure 6A:
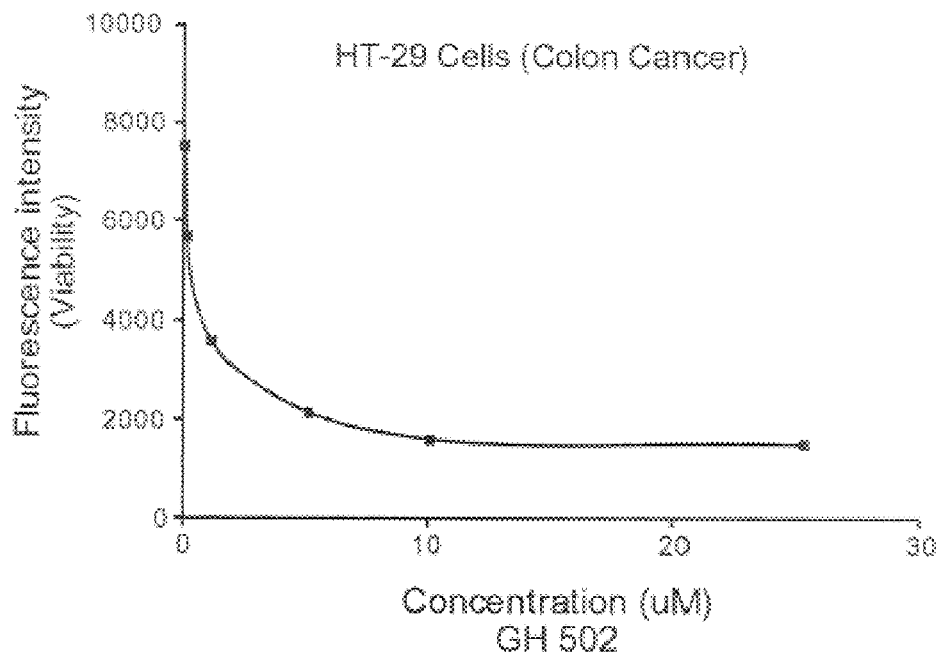
FIGS. 6A and 6B show the loss in cell viability in HT-29 colon cancer cells, in response to increasing concentrations of GH 502 (GCBH 118) (FIG. 6A), and the effect of various treatments, including increasing concentration of GH501 (GCBH 110) on U251 malignant glioma cells and BTIC EF12 brain tumor initiating stem cells (FIG. 6B).
Figure 6B:
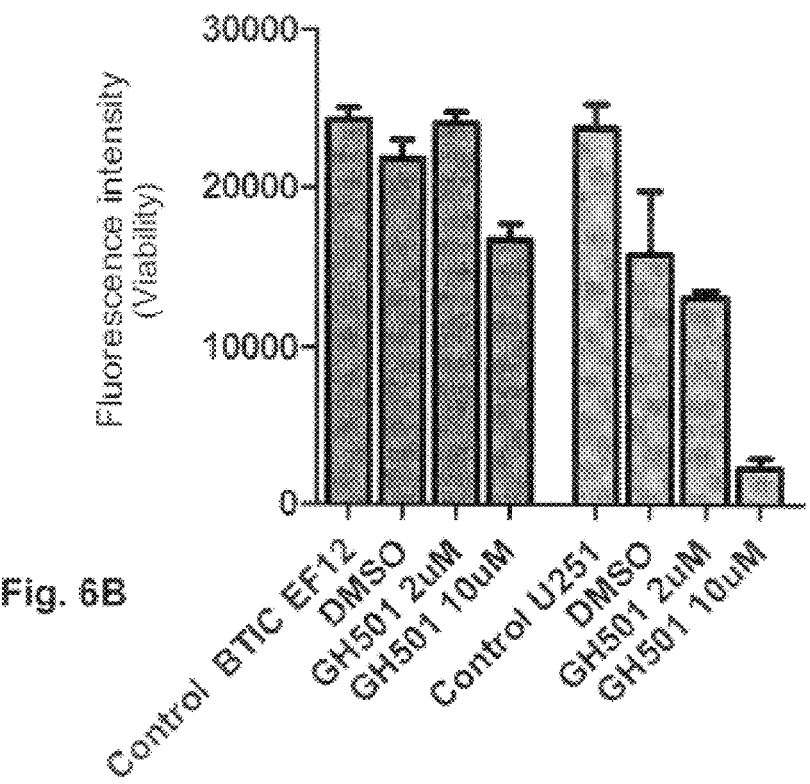

FIGS. 6A and 6B demonstrate the ability of the compounds of the invention to inhibit cell survival in both colon cancer cells (FIG. 6A) and two brain cancer cell lines: brain tumor initiating (stem) cells (BTCI EF-29) and U251, a malignant glioma cell line (FIG. 6B). The study shown in FIG. 6A examined the effect of GCBH-118 (GH502) on an HT-29 colon cancer cell, showing an $IC_{50}$ value of about 1 μM. The bar graph in FIG. 6B shows compound inhibition of the BTIC EF12 cells by GH501 (GCBH-110=B1031) at 10 μM. The graph indicates an $IC_{50}$ value for the B1031 compound against the U251 brain cancer cell line of between 2 and 10 μM.

The $IC_{50}$ values given in Tables 1-4 were measured using the B1031 (GCBH-100) compound) shown in Section IIB above. To confirm the generality of the results with respect to other fluribprofen analogs prepared in accordance with the invention, $IC_{50}$ values for the other 11 analog compounds given in Section IIB were similarly determined for the H2122 lung carcinoma cell line. The results, given in Table 5, demonstrate that all of the analogs tested, which include a wide range of amino acid groups and terminal amide groups, have comparable anti-cancer activities.

TABLE 5

| Flurbiprofen analog compound | Analogs | H2122 In vitro (uM) | Solubility |
|---|---|---|---|
| BKM-1694 HPLC = GCBH-100 | Fmba-OC2Y-Atmp | 4.0 | 50% DMSO |
| BKM-1696 HPLC = GCBH-102 | Fmba-OC2Y-Amp | 8.0 | 20% DMSO |
| BKM-1814 HPLC = GCBH-106 | Fmba-Dip-Atmp | 1.20 | 50% DMSO |
| BKM-1820 HPLC = GCBH-110 | Fmba-Bip-Atmp | 0.15 | 50% DMSO |
| BKM-1822 HPLC = GCBH-112 | Fmba-2Nal-Atmp | 1.60 | 50% DMSO |
| BKM-1826 HPLC = GCBH-114 | Fmba-Bta-Atmp | 1.20 | 50% DMSO |
| BKM-1828 HPLC = GCBH-116 | Fmba-βChA-Atmp | 2.30 | 20% DMSO |
| BKM-1830 HPLC = GCBH-118 | Fmba-3Pal-Atmp | 1.40 | H20 |
| BKM-1860 HPLC = GCBH-120 | [(S)-Fmba]-βBpa-Atmp | 5.40 | 50% DMSO |
| BKM-1866 HPLC = GCBH-122 | [(S)-Fmba]-F3MF-Atmp | 2.10 | 50% DMSO |
| BKM-1870 HPLC = GCBH-124 | [(S)-Fmba]-PFF-Atmp | 2.50 | 20% DMSO |
| BKM-1880 HPLC = GCBH-126 | [(S)-Fmba]-MEL-Atmp | 3.80 | 20% DMSO |

IIIB. Mechanism of Cell Inhibition

The studies reported in Tables 1-3 above were carried out by incubating the cells in the test compound for four days, under standard cell-culture conditions, and measuring cell survival on day 5 (see Example 2). This time period was chosen from initial studies on the change in $IC_{50}$ values recorded for the H2122 adenocarcinoma lung carcinoma cell line, when incubated with the B1031 compound over time periods up to 62 hours. The results, shown in FIG. 7, indicate that a several-day period is required for maximum cell inhibition effect.

Figure 7:
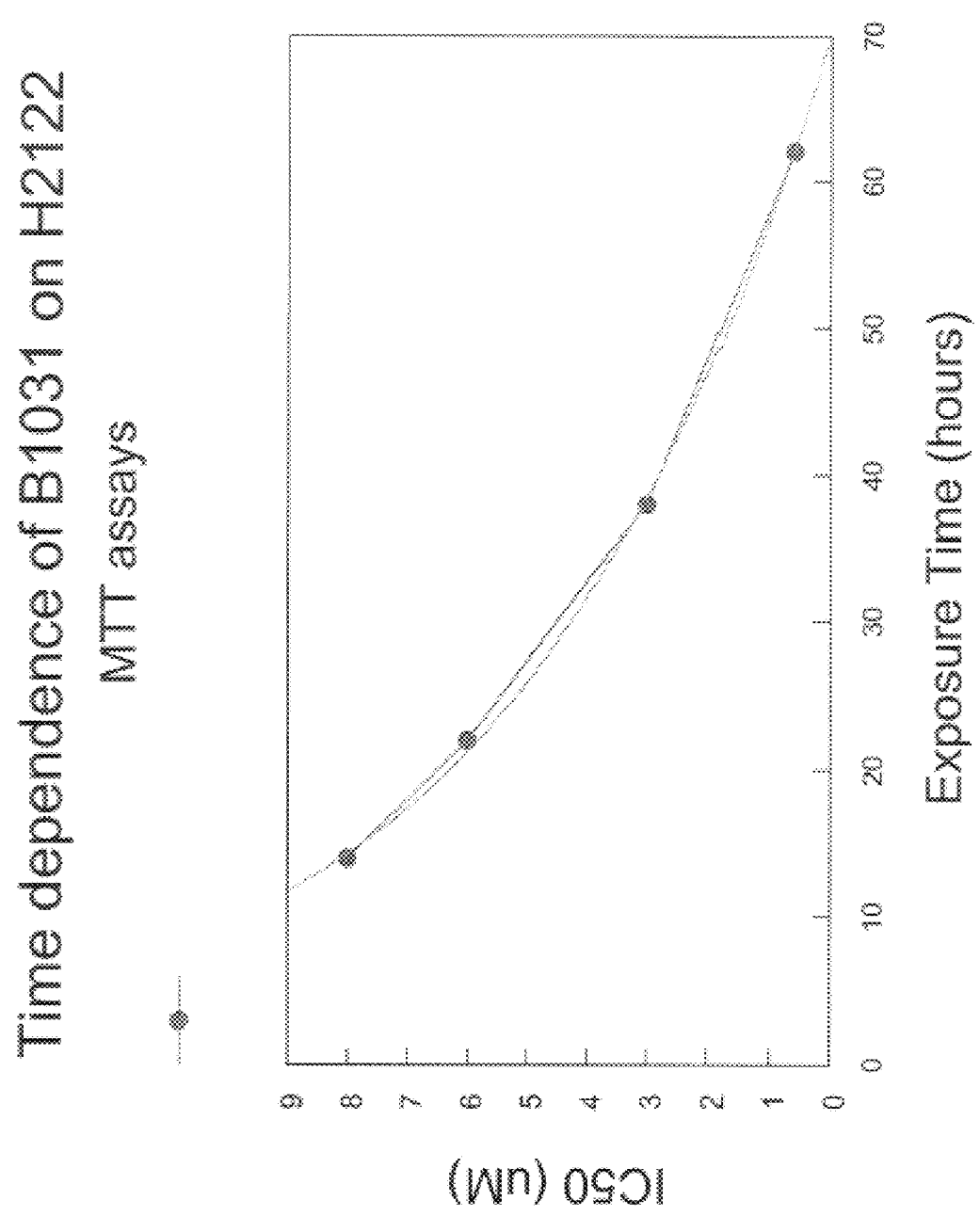
FIG. 7 shows the effect of exposure time on lung carcinoma cell line H2122 survival in refollowing treatment with N—[(S)-2-Fluoro-α-methyl-4-biphenylacetyl]-[L-(4-phenylphenyl)alanine]-N'-(2,2,6,6-tetramethyl-4-piperidinyl)amide (GCBH-110=B1031; (S)-Fmba-(L)-Bip-Atmp) using an MTT cell viability assay.
Figure 8:
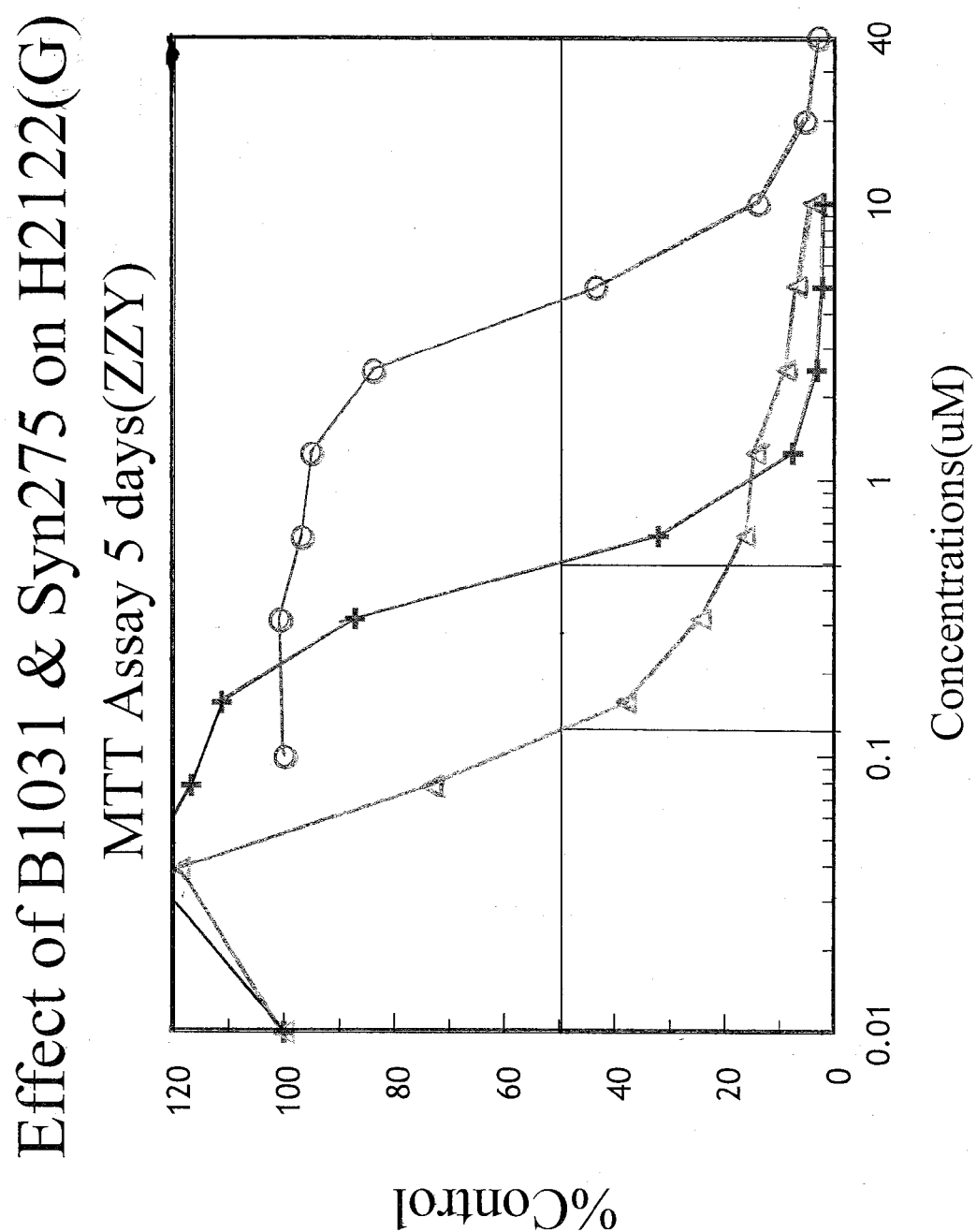
FIG. 8 compares the cytotoxic effects of B1031 with two epigenetic modulators HDACi (Syn275) and DNA demethylase inhibitor (Aza-dC) in H2122 lung cancer cell line.
Figure 10:
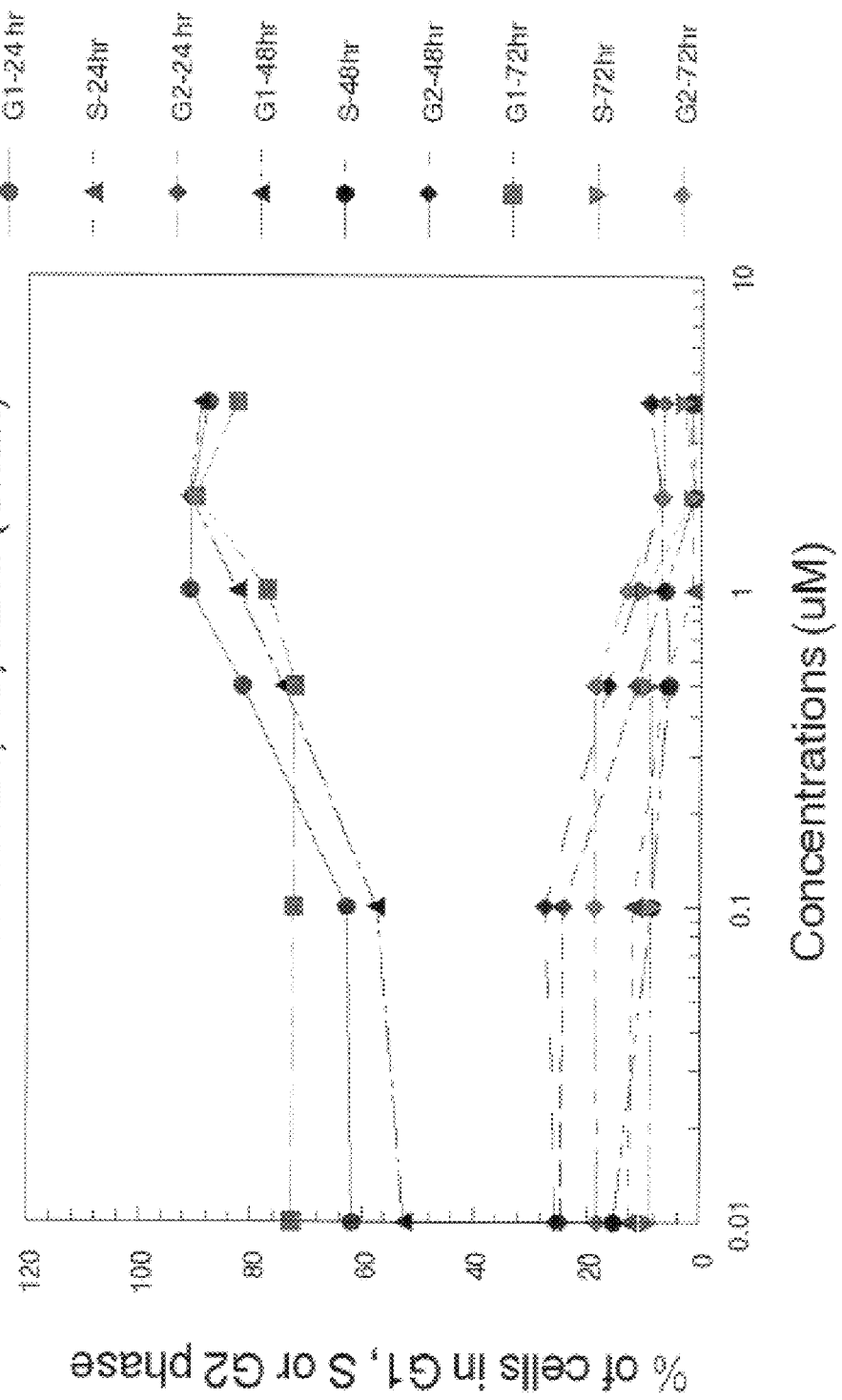
FIG. 10 is a plot showing the percentages of H122 cells G1, S, and G2 cycle at 24, 4e8, and 72 hours, as a function of B1031 concentration in the cell medium.

FIG. 10 provides an explanation of the time-dependent $IC_{50}$ values observed in FIG. 7, and insight into the mechanism by which the compounds of the invention exert their anti-cancer effect. In the study shown in FIG. 10, H2122 cells were cultured in the presence of one of the six concentrations of the B1031 compound, as indicated in the figure. At time periods 24, 48, and 72 hours after incubation with the compound, cells from each of the six cultures (having increasing concentrations of the compound), were examined for percent cells in G1, S, or G2 cell phase. The data in the figure show that (i) exposure of the cells to the compound results in marked shift of the cell populations away from the S and G2 phases to the G1 phase, and a modest dose-dependence of this effect up to about 1

These results indicate that at the compounds of the invention act, at least in part, by arresting the cells in G1 phase, preventing the cells from entering the S cell division phase. Other physical or chemical stimuli, such as interferon lambda, which are known to arrest cells in G1, are believed to produce anti-tumor effects ultimately through an apoptosis mechanism (e.g., Li. Q., et al, Eur J. Cancer, 46(1):180-190, January 2010.).

IIIC. Relative Anti-Cancer Activity of Flurbiprofen Analog Compounds

Some non-steroidal anti-inflammatory drugs (NSAIDS) are known to cause cancer cells into G1 arrest, but only at quite high concentrations, e.g., greater than 500 uM. That this known NSAID effect on cancer cells is qualitatively different from that seen with compounds of the present invention is demonstrated in FIG. 9, which shows the dose response curve of the B1031 compound and flurbiprofen with a variety of lung carcinoma cells. As seen, $IC_{50}$ values for the B1031 compound are about 1000 fold lower than those of flurbiprofen; that is, the anti-cancer activity of the B1031 compound is about 1,000 times greater than that of flurbiprofen.

Figure 9:
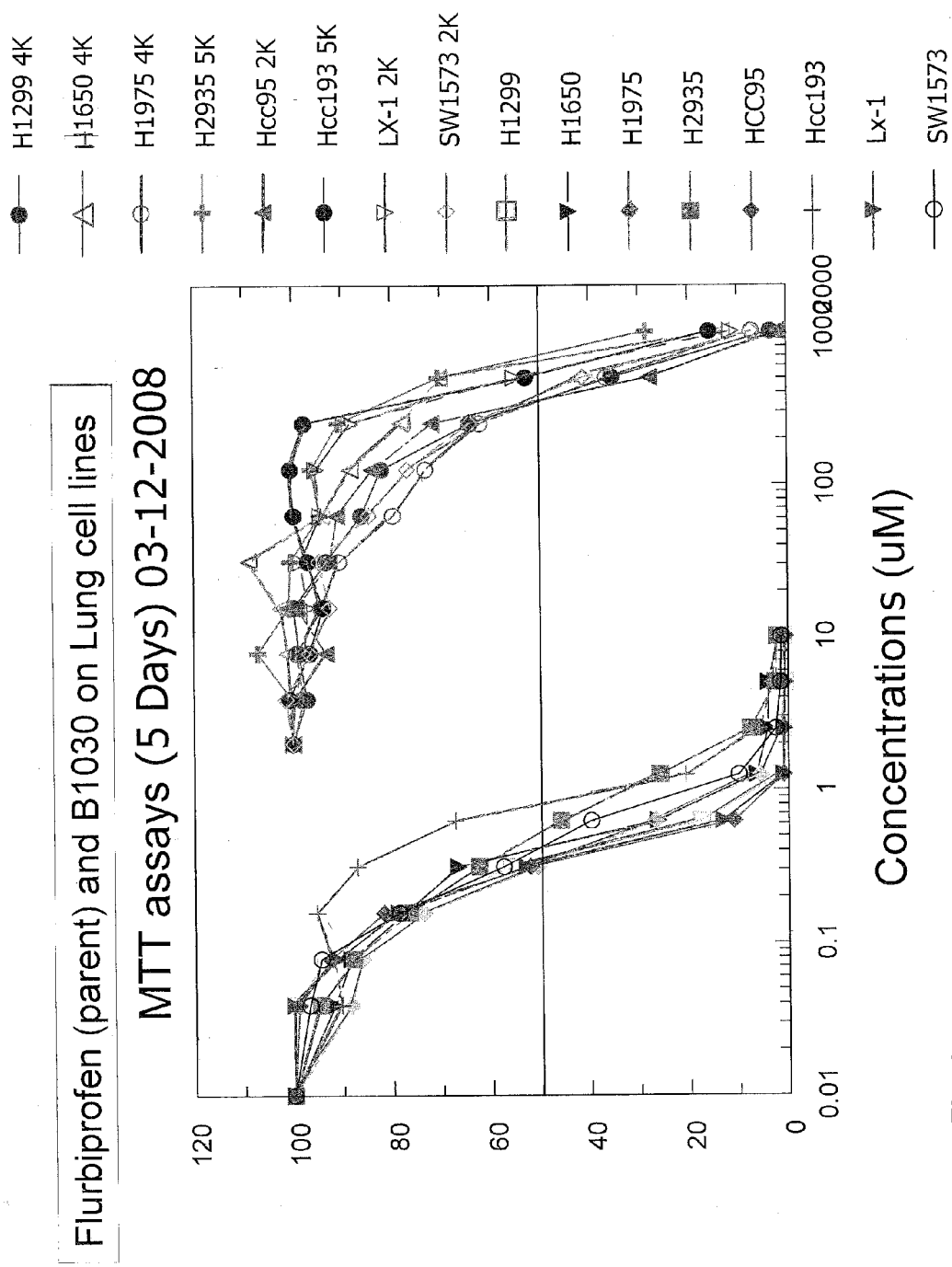
FIG. 9 compares the cytotoxic effects of B1031 with unmodified Flurbiprofen parental compound in 16 lung cancer cell lines.

FIG. 9 compares the cytotoxic effects of B1031 with two epigenetic modulators: HDACi (Syn275) and DNA demethylase inhibitor (Aza-dC) in H2122 lung cancer cell line. B1031 is many-fold more active in inhibiting H2122 cells than Aza-dC and about 4-fold less active than Syn275.

These results support a conclusion that the flurbiprofen analog compounds of the present invention are able to target and inhibit the viability of rapidly dividing cancer cells.

IV. Method of Cancer Treatment

The present invention provides methods of treating cancer in a mammal by administering a therapeutically effective amount of one of the compounds of the present invention to the mammal. These methods may include killing or inhibiting the growth of cancer cells in the mammal. These cellular effects result in reduced growth and inhibition of the malignant phenotype of the cell and ultimately, death of the cell.

More generally, the treatment method involves administering to a mammalian subject having a cancer, a therapeutically effective amount of the flurbiprofen analog compound of the invention, and repeating the compound administration at intervals of at least twice per week for a period of at least four weeks. Typically, the compound is administered every day, until a suitable end point, e.g., desired decrease in tumor volume or tumor marker, is achieved. Doses of the compound may range between about 0.5 to 50 mg/kg body weight of the treated subject. For example, the compound may be administered on a daily basis at a daily dose between 1 and 25 mg/kg body weight, typically by oral, intraperitoneal, or intravenous route.

Figure 11:
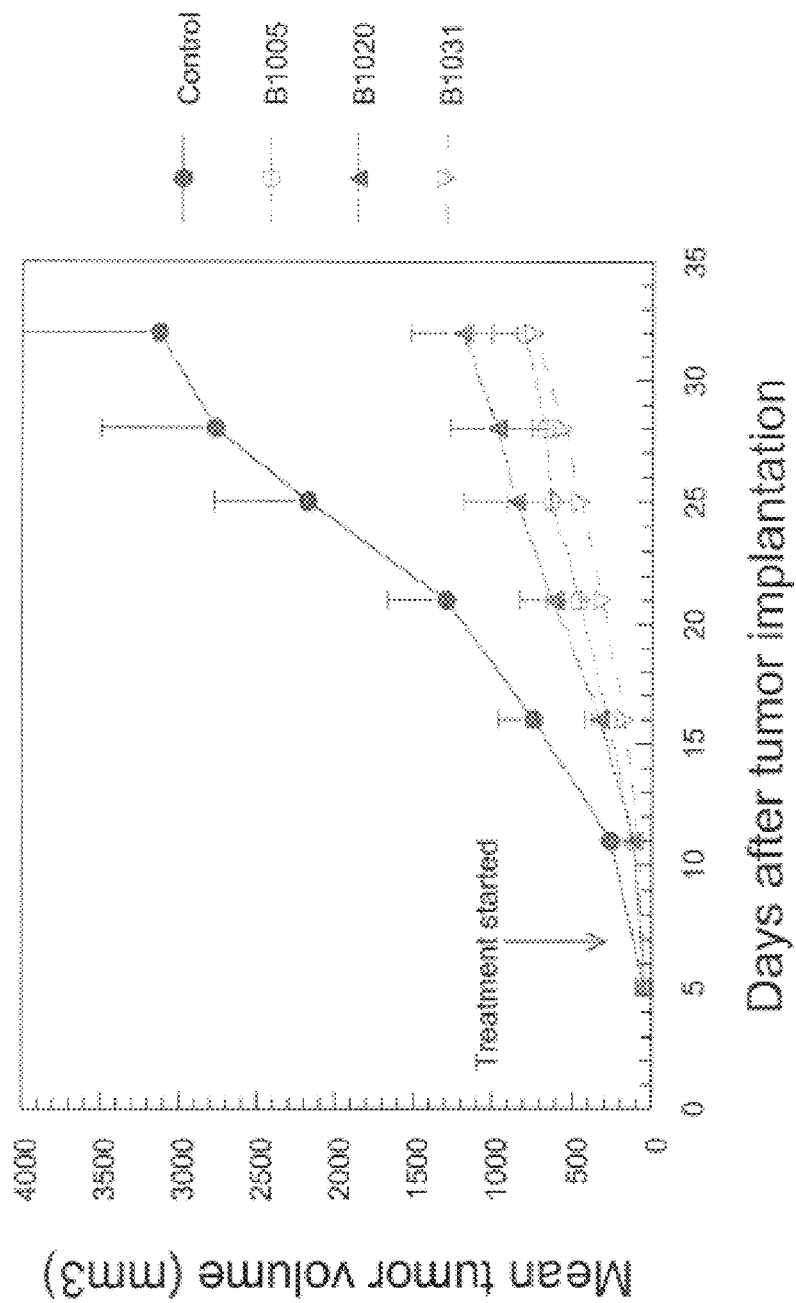
FIG. 11 shows the effect of treatment with three compounds of the present invention (GCBH-104=B1005, GCBH-108=B1020 and GCBH-110=B1031) on H2122 lung carcinoma solid tumor xenograft volume in nude mice.

The efficacy of the treatment method was examined for both lung carcinoma-cell tumors and pancreatic-cell tumors implanted in athymic mice, according to the method detailed in Example 3. In the first study, mice injected with lung-carcinoma cells were treated, seven days after cancer-cell implantation, by daily injection of 5 mg/kg body weight of one of three different flurbiprofen analog compounds: B1005 (GCBH 104); B1020 (GCBH 108) and B1031 (GCBH 110). Tumor size was measured by calipers at the days indicated in FIG. 11, with final tumor weight and volume being determined by extracting the tumor from the sacrificed animals. As seen from the data in FIG. 11, compound GCBH-104 caused a 74% inhibition of growth of the lung carcinoma cell line H2122 over the 25 days of treatment; compound GCBH-108 caused a 61% inhibition; and compound GCBH-110 caused a 76% inhibition of growth of the lung carcinoma cell tumor.

Figure 12:
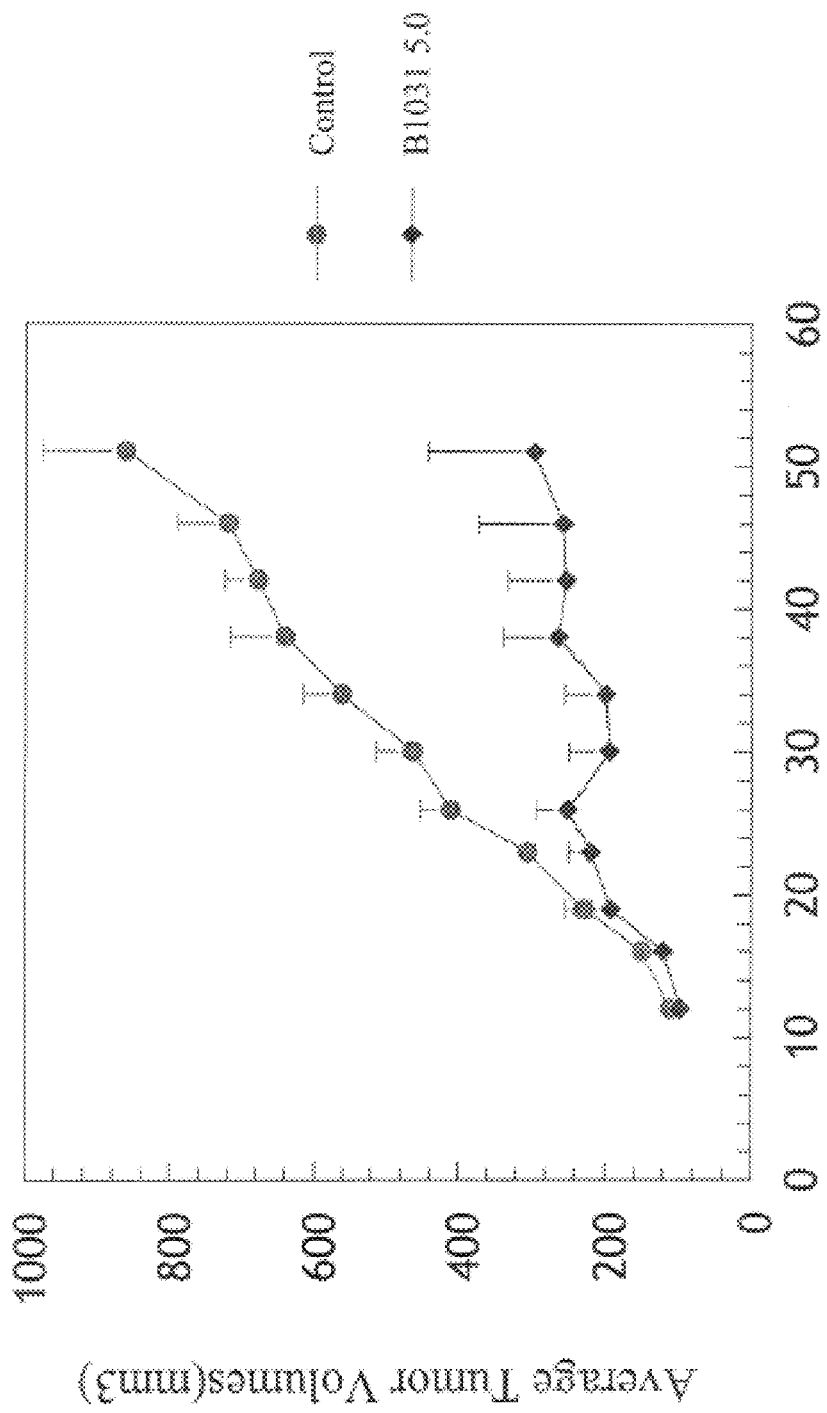
FIG. 12 shows the effect of treatment with compound GCBH-110=B1031 on MiaPaCa pancreatic carcinoma solid tumor xenograft volume in nude mice.

Similar results were obtained when the treatment method was applied to animals having pancreatic carcinoma implants, as shown in FIG. 12. Here the B1031 compound caused a 66% inhibition of pancreatic carcinoma cell line MiaPaCaPC3 tumors at a dose of 5 mg/kg/every day, beginning on the eleventh day following implantation.

The method may further include administering to the patient a second cancer therapy regimen, such as radiotherapy and/or one or more other chemotherapeutic compounds, where administering the compound of the invention is preferably effective to potentiate the effect of the second cancer therapy regimen. Such additional chemotherapeutic agents may include, for example, acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, sarmustine, semustine, tamoxifen, tegafur-uracil, temozotomide, teniposide, testolactone, thioguanine, thiotepa, topotecan, valrubicin, vinblastine, vincristine, vindesine, and vinorelbine.

The methods of treating a mammal with a cancer through the administration of the compounds of the present invention may also include the application of radiation therapy, biological therapy, phototherapy and/or surgery to the mammal.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention. Additional objects, advantages, and novel features of this invention will become apparent to those skilled in the art upon examination of the following examples thereof, which are not intended to be limiting.

Example 1

Compound Synthesis

1A: This example describes the synthesis of N—[(S)-2-Fluoro-α-methyl-4-biphenylacetyl]-[L-(4-phenylphenyl)alanine]-N-(2,2,6,6-tetramethyl-4-piperidinyl)amide (GCBH-110=B1031, (S)-Fmba-(L)-Bip-Atmp, $C_{39}H_{44}FN_3O_2$: 605.78).

To a solution of N-tert-butoxycarbonyl-(L)-(4-phenylphenyl)alanine (Boc-(L)-Bip, $C_{20}H_{23}NO_4$; 341.4 mg, 1.0 mmol), 4-amino-2,2,6,6-tetramethylpiperidine (Atmp, $C_9H_{20}N_2$; 156.27 mg=171.4 μl, 1.0 mmol), and BOP reagent (442.3 mg, 1.0 mmol) in acetonitrile or dimethylformamide (DMF, 75 ml) was added N,N-diisopropylethylamine (DIPEA, 348.4 μl, 2.0 mmol). The mixture was stirred at room temperature overnight then the solvent was removed in vacuum. The residue was partitioned between ethyl acetate (75 ml) and water (15 ml). The layers were separated and the organic phase was washed with 5% $KHSO_4$ (3×10 ml), brine (10 ml), 5% $NaHCO_3$ (3×10 ml), brine (10 ml). The organic layer was dried over anhydrous $Na_2SO_4$. The solvent was evaporated, affording a white solid product, (435.2 mg, 90.7%), N-[(1,1-dimethylethoxy)carbonyl]-[L-4-(phenylphenyl)alanine]-N-(2,2,6,6-tetramethyl-4-piperidinyl)amide (Boc-L-Bip-Atmp, $C_{29}H_{41}N_3O_3$: 479.65).

The $N^α$-Boc-group was cleaved according to the classical deprotection procedure. The Boc-compound (239.8 mg, 0.50 mmol) was dissolved in 25% TFA in dichloromethane (DCM, 50 ml). After 20 min. the solution was concentrated under reduced pressure at room temperature and the residue was lyophilized from 25 ml of $H_2O$ to give the crude product as a TFA salt [L-(4-phenylphenyl)alanine]-N-(2,2,6,6-tetramethyl-4-piperidinyl)amide, 271.9 mg, 89.5%, (L-Bip-Atmp.TFA, $C_{24}H_{33}H_3O$: 379.54+2TFA=607.6). The crude product could be purified by preparative HPLC on a C18 column. The (S)-Bip-Atmp.2TFA was dissolved in 0.5 N cold HCl (10 ml) and the solution was filtered and lyophilized to obtain the L-Bip-Atmp.2HCl salt (194.5 mg, 96.1%, $C_{24}H_{33}N_3O$: 379.54+2HCl=452.46)

To a stirred mixture of (L)-Bip-Atmp.2HCl (113.12 mg, 0.25 mmol), (S)-2-fluoro-α-methyl-4-biphenyl acetic acid (61.1 mg, 0.25 mmol) and BOP (110.5 mg, 0.25 mmol) in DMF (7.5 ml) was added DIEA (180 μl, 1.0 mmol). The mixture was stirred at room temperature overnight then the solvent was evaporated at reduced pressure. The residue was diluted with ethyl acetate (50 ml) and washed with 5% $KHSO_4$ (3×10 ml), brine (10 ml), 5% $NaHCO_3$ (3×10 ml) and brine (10 ml). After being dried over anhydrous $Na_2SO_4$, the organics were concentrated to dryness yielding the crude (S)-Fmba-(L)-Bip-Atmp. The crude product was purified by preparative HPLC on a C18 column to give the desired product after lyophilization from dioxane—$H_2O$. (143.3 mg, 79.7%, as a white solid, (S)-Fmba-(L)-Bip-Atmp.TFA, $C_{39}H_{44}FN_3O_2$+TFA=719.81).

1B. Modifications of the 1A method for producing other flurbiprofen analog compounds.

1. GCBH-100 N—[(R,S)-2-Fluoro-α-methyl-4-biphenylacetyl]-[O-(2,6,dichlorobenzyl)-L-tyrosine]-N-(2,2,6,6-tetramethyl-4-piperidinyl)amide. This compound was prepared as above, substituting N-tert-butoxycarbonyl-[O-(2,6,dichlorobenzyl)-L-tyrosine] (Boc-L-OC2Y) for (Boc-L-Bip) used in Example 1A, and substituting (R,S)-2-fluoro-α-methyl-4-biphenyl acetic acid for the (S)-2-fluoro-α-methyl-4-biphenyl acetic acid used in Example 1A.

2. CBH-102: N—[(R,S)-2-Fluoro-α-methyl-4-biphenylacetyl]-[O-(2,6,dichlorobenzyl)-L-tyrosine]-N-[3-(4-methyl-1-piperizinyl)propyl]amide. This compound was prepared as in Example 1A, substituting N-tert-butoxycarbonyl-[O-(2,6,dichlorobenzyl)-L-tyrosine] (Boc-L-OC2Y) for (Boc-L-Bip) used in Example 1A, and substituting 1-(3-Aminopropyl)-4-methylpiperizine (Amp) for the 4-amino-2,2,6,6-tetramethylpiperidine (Atmp) used in Example 1A.

3. GCBH-104=B1005, N—[R,S)-2-Fluoro-α-methyl-4-biphenylacetyl]-[L-(4-phenylphenyl)alanine]-N-(2,2,6,6-tetramethyl-4-piperidinyl)amide. This compound was prepared by substituting (R,S)-2-fluoro-α-methyl-4-biphenyl acetic acid for the (S)-2-fluoro-α-methyl-4-biphenyl acetic acid used in Example 1A.

4. GCBH-108=B1020, N—[(R)-2-Fluoro-α-methyl-4-biphenylacetyl]-[L-(4-phenylphenyl)alanine]-N-(2,2,6,6-tetramethyl-4-piperidinyl)amide. This compound was prepared by substituting (R)-2-fluoro-α-methyl-4-biphenyl acetic acid for the (S)-2-fluoro-α-methyl-4-biphenyl acetic acid used in Example 1A.

5. GCBH-112: N—[(R,S)-2-Fluoro-α-methyl-4-biphenylacetyl]-[O-(2,6,dichlorobenzyl)-L-tyrosine]-N-(2,2,6,6-tetramethyl-4-piperidinyl)amide. This compound was prepared as above, substituting N-tert-butoxycarbonyl[O-(2,6,dichlorobenzyl)-L-tyrosine] (Boc-L-OC2Y) for the (Boc-L-Bip) used in Example 1A, and substituting (RS)-2-fluoro-α-methyl-4-biphenyl acetic acid for the (S)-2-fluoro-α-methyl-4-biphenyl acetic acid used in Example 1A.

6. GCBH-114: N—[(R,S)-2-Fluoro-α-methyl-4-biphenylacetyl]-(L-3-benzothienylalanine)-N-(2,2,6,6-tetramethyl-4-piperidinyl)amide. This compound was prepared as above, substituting N-tert-butoxycarbonyl-(L-3-benzothienylalanine) (Boc-L-Bta) for the (Boc-L-Bip) used in Example 1A, and substituting (RS)-2-fluoro-α-methyl-4-biphenyl acetic acid for the (S)-2-fluoro-α-methyl-4-biphenyl acetic acid used in Example 1A.

7. GCBH-116: N—[(R,S)-2-Fluoro-α-methyl-4-biphenylacetyl]-(β-cyclohexyl-L-alanine)-N-(2,2,6,6-tetramethyl-4-piperidinyl)amide. This compound was prepared as above, substituting N-tert-butoxycarbonyl-(β-cyclohexyl-L-alanine) (Boc-L-βCha) for the (Boc-L-Bip) used in Example 1A, and substituting (RS)-2-fluoro-α-methyl-4-biphenyl acetic acid for the (S)-2-fluoro-α-methyl-4-biphenyl acetic acid used in Example 1A.

8. GCBH-118: N—[(R,S)-2-Fluoro-α-methyl-4-biphenylacetyl]-(β-3-pyridyl-L-alanine)-N-(2,2,6,6-tetramethyl-4-piperidinyl)amide. This compound was prepared as above, substituting N-tert-butoxycarbonyl-(β-3-pyridyl-L-alanine) (Boc-L-3Pal) for the (Boc-L-Bip) used in Example 1A, and substituting (RS)-2-fluoro-α-methyl-4-biphenyl acetic acid for the (S)-2-fluoro-α-methyl-4-biphenyl acetic acid used in Example 1A.

9. GCBH-120: N—[(S)-2-Fluoro-α-methyl-4-biphenylacetyl]-[R,S,-β-(p-biphenyl)-β-alanine]-N-(2,2,6,6-tetramethyl-4-piperidinyl)amide. This compound was prepared as above, substituting N-tert-butoxycarbonyl-[R,S)-β-biphenyl)-β-alanine] (Boc-(R,S)-βBpa) for the (Boc-L-Bip) used in Example 1A.

10. GCBH-122: N—[(S)-2-Fluoro-α-methyl-4-biphenylacetyl]-[(4-trifluoromethyl)-L-phenylalanine]-N-(2,2,6,6-tetramethyl-4-piperidinyl)amide. This compound was prepared as above, substituting N-tert-butoxycarbonyl-[(4-trifluoromethyl)-L-phenylalanine] (Boc-L-F3MF) for the (Boc-L-Bip) used in Example 1A.

11. GCBH-124: N—[(S)-2-Fluoro-α-methyl-4-biphenylacetyl]-[(4-fluoro)-L-phenylalanine]-N-(2,2,6,6-tetramethyl-4-piperidinyl)amide. This compound was prepared as above, substituting N-tert-butoxycarbonyl-[(4-fluoro)-L-phenylalanine] (Boc-L-PFF) for the (Boc-L-Bip) used in Example 1A.

12. GCBH-126: N—[(S)-2-Fluoro-α-methyl-4-biphenylacetyl]-[(4-bis-(2-chloroethyl)amino-L-phenylalanine]-N-(2,2,6,6-tetramethyl-4-piperidinyl)amide. This compound was prepared as above, substituting N-tert-butoxycarbonyl-[(4-bis-(2-chloroethyl)amino-L-phenylalanine] (Boc-L-MEL) for the (Boc-L-Bip) used in Example 1A.

Example 1 illustrate the synthesis of compounds having different $R_4$ and $R_5$ groups, and different stereoisomers of the flurbiprofen moiety. It will be appreciated that desired variations in $R_1$, $R_2$, and/or $R_3$ can be made by substituting for the (R, S, or R,S)-2-fluoro-α-methyl-4-biphenyl acetic acid used in the above syntheses, flurbiprofen analogs having different R groups at the $R_1$, $R_2$, and/or $R_3$ positions. It will also be appreciated how compounds in which $C(O)R_5$ is an ester can be formed, by initially reacting substituting an alcohol for the amine used in forming the initial BOC-protected amino-acid amide compound, in accordance with well-known methods in organic synthesis.

Example 2

Inhibition of Cancer Cell Viability by Flubiprofen Analog Compounds

Cell growth and survival following treatment with N—[(S)-2-Fluoro-α-methyl-4-biphenylacetyl]-[L-(4-phenylphenyl)alanine]-N-(2,2,6,6-tetramethyl-4-piperidinyl) amide (GCBH-110=B1031; (S)-Fmba-L-Bip-Atmp) were measured by a rapid colorimetric assay based on the tetrazolium salt MTT (3-(4,5-dimethylthiazol-2-yl)-2,5-diphenyl tetrazolium bromide) (Mosmann, J. Immunol. Methods 65: 55-63, 1983, with minor modifications).

Briefly, approximately 1,000-5,000 cancer cells from 15 different cancer cells lines were plated in 100 µL of growth medium in 96-well flat-bottomed microtiter plates. Cells were incubated overnight to allow recovery. Compounds to be tested were added to the cells in triplicate in a range of concentrations and the cells were incubated at 37° C., 5% CO2, with 100% humidity. Control cells were treated in the same way without antagonists. All wells had a final volume of 200 µL. Plates were incubated for 4 days, allowing sufficient time for cell replication and compound-induced cell death to occur. On day 5, 25 µL of a 2 mg/mL solution of MTT (Sigma) dissolved in RMPI-1640 was added to each well. The plate was incubated for 4 h at 37° C. The supernatant liquid was removed and the blue formazan complex was dissolved by adding 100 µL of 0.02 N HCl in 75% isopropanol to all wells. Absorbance was immediately determined using a scanning multiwell plate reader. As seen in FIG. 1, GCBH=B1031 caused 50% cell death in the several cancer cell lines tested at concentrations between about 0.1 µM and about 1 µM under these conditions (FIG. 1).

Similarly, cell growth and survival following treatment with GCBH-110=B1031 was tested using the same MTT assay in 17 lung cancer cell lines. GCBH-110=B1031 caused 50% cell death at concentrations between about 0.1 µM and about 2 µM under these conditions (FIG. 2).

Figure 3:
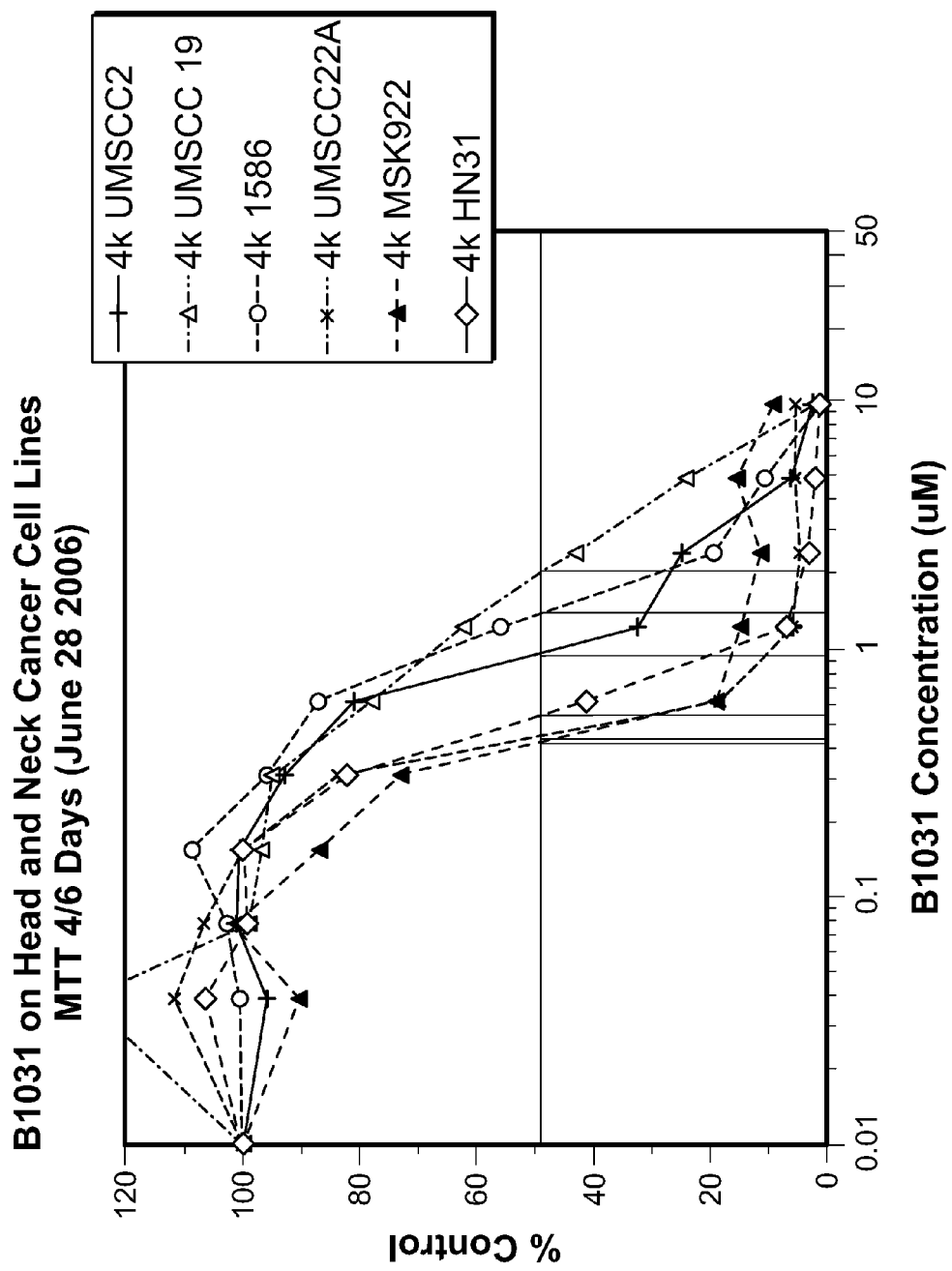
FIG. 3 show cell survival of 6 head and neck cancer cell lines following treatment with N—[(S)-2-Fluoro-α-methyl-4-biphenylacetyl]-[L-(4-phenylphenyl)alanine]-N'-(2,2,6,6-tetramethyl-4-piperidinyl)amide (GCBH-110=B1031; (S)-Fmba-(L)-Bip-Atmp) using an MIT cell-viability assay.
Figure 4:
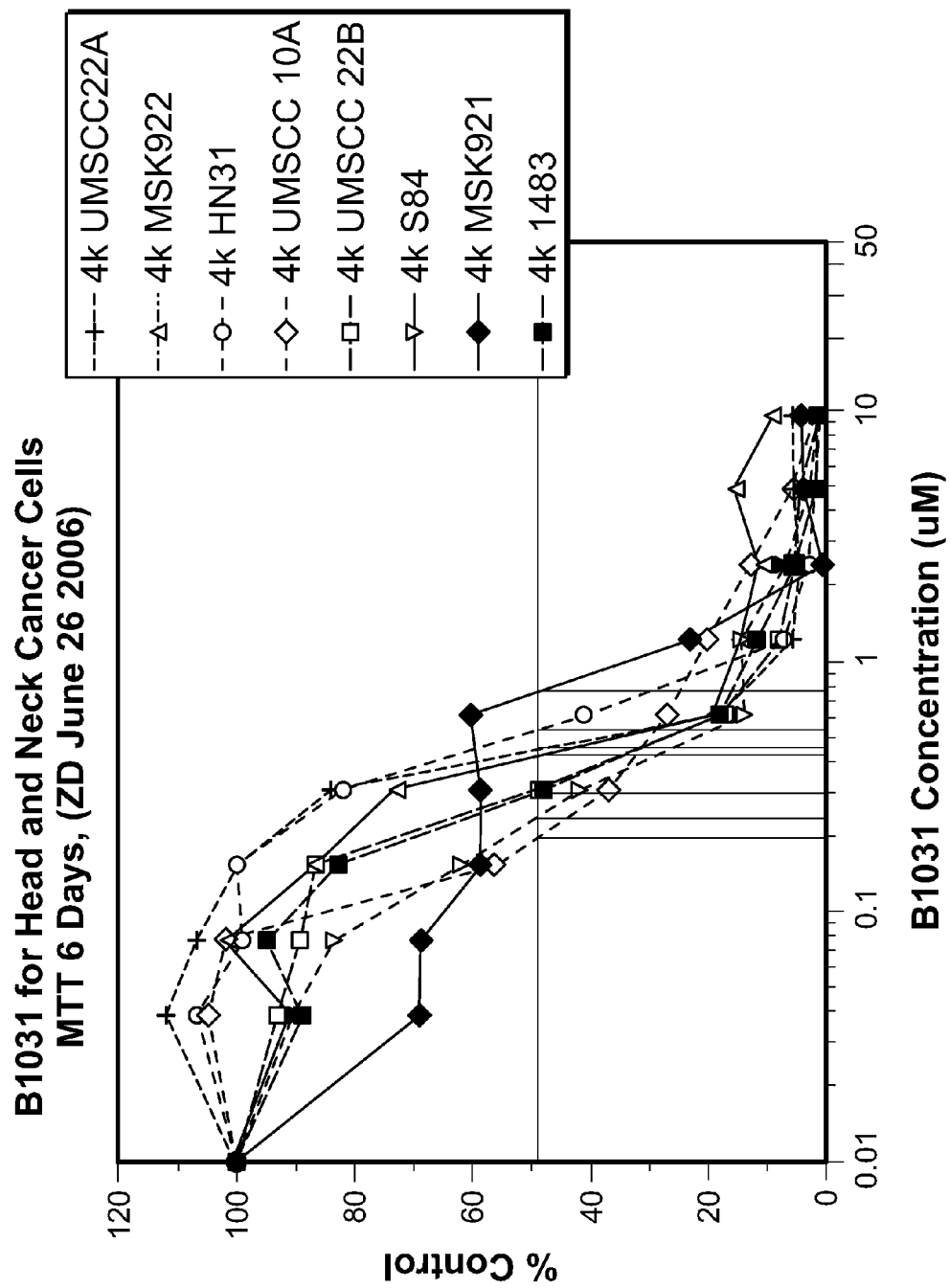
FIG. 4 shows cell survival of 8 head and neck cancer cell lines following treatment with N—[(S)-2-Fluoro-α-methyl-4-biphenylacetyl)]-[L-(4-phenylphenyl)alanine]-N'-(2,2,6,6-tetramethyl-4-piperidinyl)amide (GCBH-110=B1031; (S)-Fmba-(L)-Bip-Atmp) using an MTT cell-viability assay.

Similarly, cell growth and survival following treatment with GCBH-110=B1031 was tested using the same MTT assay in 6 head and neck cancer cell lines. GCBH-110=B1031 caused 50% cell death at concentrations between about 0.3 µM and about 2 µM under these conditions (FIG. 3). These results were repeated with another panel of head and neck cancer cell lines using a longer treatment exposure to GCBH-110=B1031 (FIG. 4). GCBH-110=B1031 caused 50% cell death at concentrations between about 0.2 µM and about 0.8 µM under these conditions.

Example 3

Inhibition of Tumor Growth In Vivo in Nude Mice

Compounds having high in vitro cytotoxic activity were tested against implanted tumors in vivo. In one study, athymic nude mice were implanted subcutaneously with suspensions of approximately 2 million H2122 lung carcinoma cells, in Matrigel suspension. On the seventh day after tumor implantation, groups of 5 mice bearing implants were injected intraperitoneally with the compounds being tested at 5 mg/kg/ every day; control animals were injected with an equal volume of isotonic saline. Less soluble compounds were initially dissolved in dimethyl sulfoxide (DMSO) and diluted with medium. In those cases the control injections contained the same concentration of DMSO. Tumor size was measured with a caliper three times per week. Tumor volume was calculated by the formula:

$$\text{Volume (cc)} = 3.14 \times (\text{length}) \times (\text{width})^2/6$$

At autopsy, tumors were removed and weighed. Tumor inhibition was calculated on both weight and measurement basis.

In a second study, athymic nude mice were implanted subcutaneously with suspensions of approximately 2 million MiaPaCa pancreatic carcinoma cells, in Matrigel suspension. On the 12th day after tumor implantation, groups of 5 mice bearing implants were injected intraperitoneally with the B1031 compound at 5 mg/kg/every day; control animals were injected with an equal volume of isotonic saline. The compound was initially dissolved in dimethyl sulfoxide (DMSO) and diluted with medium. Tumor size was measured with a caliper three times per week, and tumor volume calculated as above. At autopsy, tumors were removed and weighed. Tumor inhibition was calculated on both weight and measurement basis, with the results given in FIG. 12.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A compound having the structural formula:

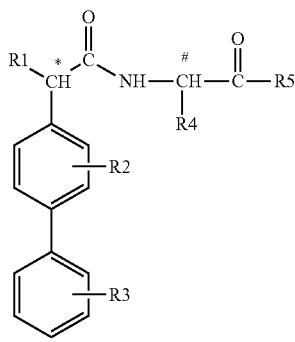

including pharmaceutically acceptable salts thereof, where
$R_1$ is selected from H or a 1-4 carbon alkyl,
$R_2$ is selected from F, Cl, and Br and may include two or more $R_2$ substitutions on the ring,
$R_3$ is selected from H, F, Cl and Br, and may include two or more non-H substitutions on the ring,
—NH—CH($R_4$)—C(O)— is a hydrophobic amino acid residue, and
$R_5$ is 1-(3-Aminopropyl)-4-methylpiperazine (Amp) or 4-Amino-2,2,6,6-tetramethylpiperidine (Atmp).

2. The compound of claim 1, wherein —NH—CH($R_4$)—C(O)— is selected from the group consisting of (4-Phenylphenyl)alanine) (Bip), 3,3-Diphenylalanine (Dip), O-(2,6-dicholorbenzyl)-tyrosine (OC2Y), 3-(2-Naphthyl)alanine (2Nal), 3-Benzothienylalanine (Bta), β-Cyclohexylalanine (βCha), 3-Pyridylalanine (3 Pal), β-(p-Biphenylyl)-β-alanine (βBpa), 4-Trifluoromethylphenylalanine (F3MF), luorophenylalanine(PFF), and Melphalane (MEL).

3. The compound of claim 1, wherein $R_2$ is a single meta-position F.

4. The compound of claim 1, wherein $R_3$ is H.

5. The compound of claim 1, wherein $R_1$ is $CH_3$.

6. The compound of claim 1, having the structure

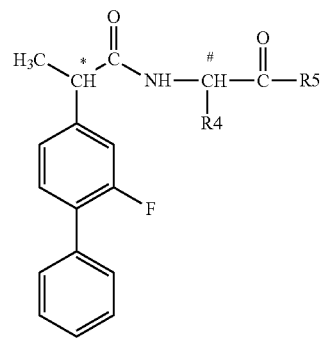

wherein —NH—CH($R_4$)—C(O)— is selected from the group consisting of (4-Phenylphenyl)alanine) (Bip), 3,3-Diphenylalanine (Dip), O-(2,6-dicholorbenzyl)-tyrosine (OC2Y), 3-(2-Naphthyl)alanine (2Nal), 3-Benzothienylalanine (Bta), β-Cyclohexylalanine (βCha), 3-Pyridylalanine (3 Pal), β-(p-Biphenylyl)-β-alanine (βBpa), 4-Trifluoromethylphenylalanine (F3MF), luorophenylalanine (PFF), and Melphalane (MEL).

7. The compound of claim 1, which is a pure R or S enantiomer or an RS racemic mixture at the chiral position * and a pure L or pure D enantiomer or an LD racemic mixture at the chiral position #.

8. The compound of claim 1, which is a pure S enantiomer at the chiral position * and a pure S enantiomer at the chiral position #.

9. A pharmaceutical composition containing the compound of claim 1 in a pharmaceutically acceptable medium suitable for oral or parenteral administration.

10. A method of treating a solid tumor in a mammalian subject wherein the cancer is pancreatic or lung cancer, comprising administering to the subject a therapeutically effective amount of compound of claim 1, and repeating said administration at intervals of at least twice per week for a period of at least four weeks.

11. The method of claim 10, wherein said compound is administered on a daily basis at a daily dose between 1 and 25 mg/kg body weight.

12. The method of claim 10, wherein said compound is administered orally, intraperitoneally, intravenously, or intranasally or by inhalation.

13. The method of claim 10, which further includes administering to the subject a second cancer therapy regimen selected from radiotherapy and one or more other chemotherapeutic compounds.

14. The method of claim 13, wherein administering the compound is effective to potentiate the effect of the second cancer therapy regimen.

15. The method of claim 10, wherein the compound administered is the compound of claim 9.

16. The method of claim 10, wherein said administering includes administering the compound at a daily dose between 1 and 25 mg/kg body weight of the compound over a period of at least five weeks.

17. A compound having a structural formula selected from the group consisting of:
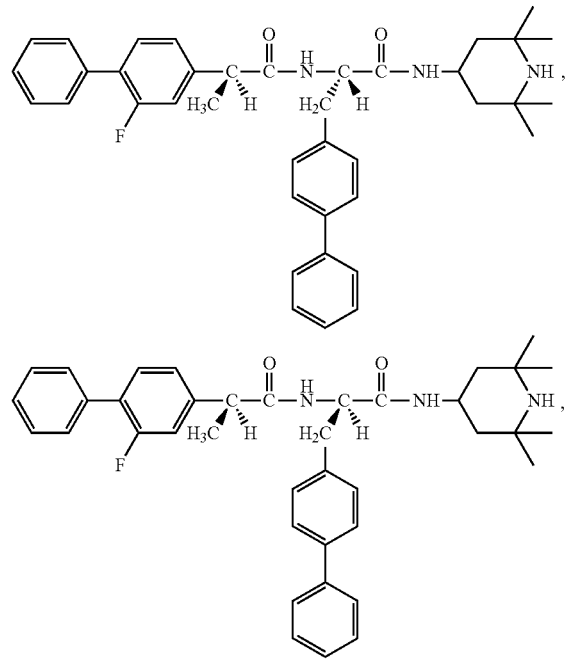
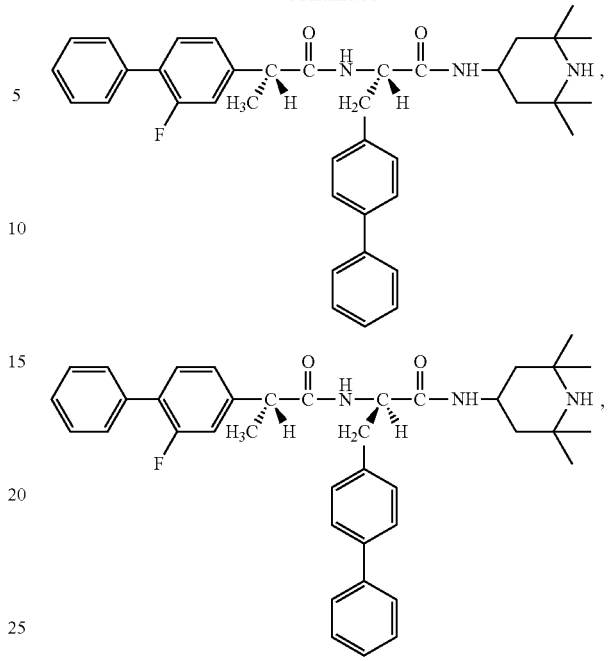
and pharmaceutically acceptable salts thereof.
* * * * *